United States Patent
DeShazo et al.

(10) Patent No.: US 11,154,714 B2
(45) Date of Patent: Oct. 26, 2021

(54) CAPACITIVE VOLTAGE MULTIPLIER FOR PROVIDING ADJUSTABLE CONTROL DURING A STIMULATION PULSE

(71) Applicant: ADVANCED NEUROMODULATION SYSTEMS, INC., Plano, TX (US)

(72) Inventors: Daran DeShazo, Lewisville, TX (US); Steven Boor, Plano, TX (US); Gavin L. Rade, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 148 days.

(21) Appl. No.: 16/520,052

(22) Filed: Jul. 23, 2019

(65) Prior Publication Data
US 2021/0023373 A1    Jan. 28, 2021

(51) Int. Cl.
*A61N 1/36*  (2006.01)
*A61N 1/378* (2006.01)
*A61N 1/372* (2006.01)

(52) U.S. Cl.
CPC ..... *A61N 1/36062* (2017.08); *A61N 1/36071* (2013.01); *A61N 1/3787* (2013.01); *A61N 1/37211* (2013.01)

(58) Field of Classification Search
CPC .............. A61N 1/36062; A61N 1/3787; A61N 1/36071; A61N 1/37211; A61N 1/36125; A61N 1/36153; H02M 3/07
See application file for complete search history.

(56) References Cited

U.S. PATENT DOCUMENTS

| 5,222,494 | A  | * | 6/1993 | Baker, Jr. ........... A61N 1/36128 607/118 |
| 5,423,866 | A  |   | 6/1995 | Ekwall |
| 6,609,031 | B1 |   | 8/2003 | Law et al. |
| 7,212,110 | B1 |   | 5/2007 | Martin et al. |
| 7,228,179 | B2 |   | 6/2007 | Campen et al. |
| 7,571,007 | B2 | * | 8/2009 | Erickson ............. A61N 1/3787 607/61 |
| 8,446,212 | B2 |   | 5/2013 | Tranchina et al. |
| 9,844,661 | B2 |   | 12/2017 | Franz et al. |

(Continued)

FOREIGN PATENT DOCUMENTS

| EP | 2924878 A1 * | 9/2015 | ......... H03F 3/45183 |
| WO | 2001093953 A1 | 12/2001 | |
| WO | 2005101627 A1 | 10/2005 | |

OTHER PUBLICATIONS

ISA/US, International Search Report and Written Opinion, Application No. PCT/US2020/039296, dated Sep. 14, 2020, 15 pgs.

*Primary Examiner* — Catherine M Voorhees
(74) *Attorney, Agent, or Firm* — Norton Rose Fulbright US LLP

(57) ABSTRACT

An implantable medical device (IMD) includes an adjustable capacitive voltage multiplier (CVM) that is responsive to diagnostic circuitry configured to provide control signals within a single stimulation current pulse for adjusting the voltage output applied to an electrode of the IMD's lead system. A control counter is coupled to the diagnostic circuitry for incrementing or decrementing an N-bit counter output signal operative to reconfigure a charge pump arrangement of the CVM so as to facilitate an adjusted voltage output.

20 Claims, 11 Drawing Sheets

(56) References Cited

U.S. PATENT DOCUMENTS

| | | | |
|---|---|---|---|
| 2004/0210271 A1* | 10/2004 | Campen | A61B 17/3468 |
| | | | 607/48 |
| 2006/0170486 A1 | 8/2006 | Tranchina et al. | |
| 2009/0048643 A1 | 2/2009 | Erickson et al. | |
| 2009/0204160 A1 | 8/2009 | Tranchina et al. | |
| 2009/0326608 A1 | 12/2009 | Huynh et al. | |
| 2011/0072657 A1 | 3/2011 | Swanson et al. | |
| 2011/0125220 A1* | 5/2011 | Black | A61N 1/378 |
| | | | 607/59 |
| 2012/0286841 A1 | 11/2012 | Tranchina et al. | |
| 2014/0343564 A1 | 11/2014 | Feler et al. | |
| 2018/0008821 A1 | 1/2018 | Gonzalez et al. | |
| 2018/0318587 A1 | 11/2018 | Hadjiyski | |

* cited by examiner

CAPACITIVE VOLTAGE MULTIPLIER FOR PROVIDING ADJUSTABLE CONTROL DURING A STIMULATION PULSE

TECHNICAL FIELD

The present disclosure generally relates to implantable pulse generators and power supply circuitry used in association with neurostimulation systems (NS) including but not limited to spinal cord stimulation (SCS) systems.

BACKGROUND

The use of electronic stimulation systems to control pain or other indications, or to otherwise provide therapy, by nerve or muscle stimulation has been in use for a number of years. For example, spinal cord stimulation (SCS) is a technique that has been used for pain management since the 1960s. Stimulation systems may also be used in stimulating areas other than the spinal cord, such as for deep brain stimulation, muscle stimulation, etc.

Stimulation systems often comprise a pulse generator coupled to one or more therapy delivery leads having a plurality of electrodes disposed in an area in which neurostimulation is desired. Alternatively, stimulation systems may comprise a micro-stimulation system in which a small implantable housing having electrodes thereon includes a pulse generator, wherein the entire micro-stimulation system is disposed in an area in which neurostimulation is desired. Of course, all or a portion of a stimulation system need not be implanted into a body to provide a desired therapy.

A stimulation system pulse generator may be provided in various configurations, such as a totally implanted pulse generator (IPG) or a radio frequency (RF)-based system. A typical IPG configuration comprises a surgically implanted, internally-powered pulse generator and one or more mufti-electrode leads. A typical RF system configuration comprises a surgically implanted, passive receiver and a transmitter which is worn externally. In operation, the transmitter communicates, through an RF signal, to the implanted receiver to provide stimulation energy and control.

In an SCS application, electrodes used with an example pulse generator, such as any of the foregoing pulse generators, deliver a particularized electric field to a specific region of the spinal cord or surrounding tissue. Applying such an electric field across one or more nerve bundles and/or nerve roots, if property directed and produced at the necessary levels, can "mask" certain forms of chronic pain. Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the properties of an electric pulse waveform, which may generally include a stimulation frequency, a stimulation pulse width, a stimulation pulse amplitude, discharge method, and phase information, etc. (collectively "stimulation settings" or "stimsets").

Whereas advances in IPG systems and associated power supply circuitry for use with NS systems continue to grow apace, several lacunae remain, thereby requiring further innovation as will be set forth hereinbelow.

SUMMARY

Embodiments of the present patent disclosure are broadly directed to IPG systems and associated power supply circuitry wherein an adjustable capacitive voltage multiplier (CVM) is provided that is responsive to diagnostic circuitry configured to provide control signals within a single stimulation current pulse for adjusting the CVM voltage output applied to an electrode of the IPG's lead system. A control counter may be coupled to the diagnostic circuitry for incrementing or decrementing an N-bit counter output signal responsive to the control signals, wherein the N-bit counter output signal is operative to reconfigure a charge pump arrangement of the CVM so as to facilitate an adjusted voltage output.

In one aspect, an embodiment of the present patent disclosure is directed to a method for providing adjustable intra-pulse voltage multiplier control in an implantable medical device (IMD). The claimed embodiment comprises, inter alia, initializing a charge pump arrangement of a CVM disposed in the IMD to generate a target voltage at a CVM output node, connecting the CVM output node to a first electrode of an implantable lead system of the IMD, the implantable lead system having one or more leads, wherein each lead includes a plurality of electrodes and the implantable lead system is positioned proximate to a patient's tissue, and commencing delivery of a stimulation current pulse to the tissue. Responsive to determining that a control signal is received from one or more diagnostic circuits associated with the implantable lead system of the IMD while the stimulation current pulse is being delivered, following operations are performed: (a) disconnecting the CVM output node from the first electrode of the implantable lead system; (b) maintaining an auxiliary voltage source connection with the first electrode while the CVM output node is disconnected; (c) reconfiguring the charge pump arrangement based on the control signal to adjust the target voltage to be output; and (d) reconnecting the CVM output node to provide an adjusted target voltage to the first electrode of the implantable lead system. In one variation, an N-bit digital logic signal from a control counter may be provided to configure or reconfigure the charge pump arrangement, which may comprise a plurality of configurably connectable capacitors. In one variation, the charge pump arrangement may be initialized in response to a preset configuration value loaded from a register storage into the control counter. In one variation, the method may further comprise providing a storage capacitor to operate as the auxiliary voltage source connection with the first electrode for maintaining a voltage supply while the CVM is disconnected during the stimulation current pulse. In one variation, the method may further comprise continuing to deliver the stimulation current pulse to the implantable lead system; and if additional control signals are received from the diagnostic circuits before the stimulation current pulse is ended, continuing to adjust the target voltage output from the CVM according to the additional control signals and applying corresponding adjusted target voltages to the first electrode of the implantable lead system by performing the foregoing operations (a)-(d) for each adjustment.

In another aspect, an embodiment of an IMD configured to provide adjustable intra-pulse voltage multiplier control in stimulation therapy is disclosed. The claimed IMD comprises, inter ala, a capacitive voltage multiplier (CVM) circuit having a charge pump arrangement configured to generate an adjustable target voltage at a CVM output node, a control counter adapted to generate an N-bit digital logic signal operative to configure the charge pump arrangement for facilitating adjustment of the target voltage generated at the CVM output node, a register for storing a preset configuration value operative to be loaded into the control counter for initializing the charge pump arrangement, a lead system comprising one or more leads configured to be positioned proximate to a patient's tissue, wherein each lead includes a plurality of electrodes, and diagnostic circuitry operative to generate one or more control signals while a stimulation current pulse is being delivered to the lead system after the output node having an initial target voltage is connected to a first electrode of the lead system. In one representative arrangement, the diagnostic circuitry is operative to generate a control signal configured to cause one or more operations: (a) disconnecting the CVM output node from the first electrode of the implantable lead system; (b) maintaining an auxiliary voltage source connection with the first electrode while the CVM output node is disconnected; (c) reconfiguring the charge pump arrangement based on incrementing or decrementing the N-bit digital logic signal of the control counter to adjust the target voltage; and (d) reconnecting the CVM output node to provide an adjusted target voltage to the first electrode of the implantable lead system.

In one variation, the CVM's charge pump arrangement may comprise a plurality of capacitors configurably connectable responsive to the N-bit digital logic output signal from the control counter. In one variation, an embodiment of the IMD may comprise a capacitor selectably connectable as the auxiliary voltage source connection with the first electrode for maintaining a voltage supply while the CVM is disconnected during the stimulation current pulse. In one variation, an embodiment of the diagnostic circuitry of the IMD may comprises a circuit for generating a DOWN signal operative as the control signal in response to determining that a voltage at a second electrode of the lead system operative as a return terminal across the patient's tissue is greater than a reference voltage, wherein the DOWN signal is operative to decrement the control counter to cause a decrease in the target voltage by a first predetermined amount. In one variation, an embodiment of the diagnostic circuitry of the IMD may comprise a circuit for generating an UP signal operative as the control signal in response to determining that a voltage at an output node of a current regulator of the IMD is within a range of a power supply rail voltage provided to the current regulator, wherein the UP signal is operative to increment the control counter to cause an increase in the target voltage by a second predetermined amount.

Additional/alternative features, variations and/or advantages of the embodiments will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

DETAILED DESCRIPTION

Figure 1A:
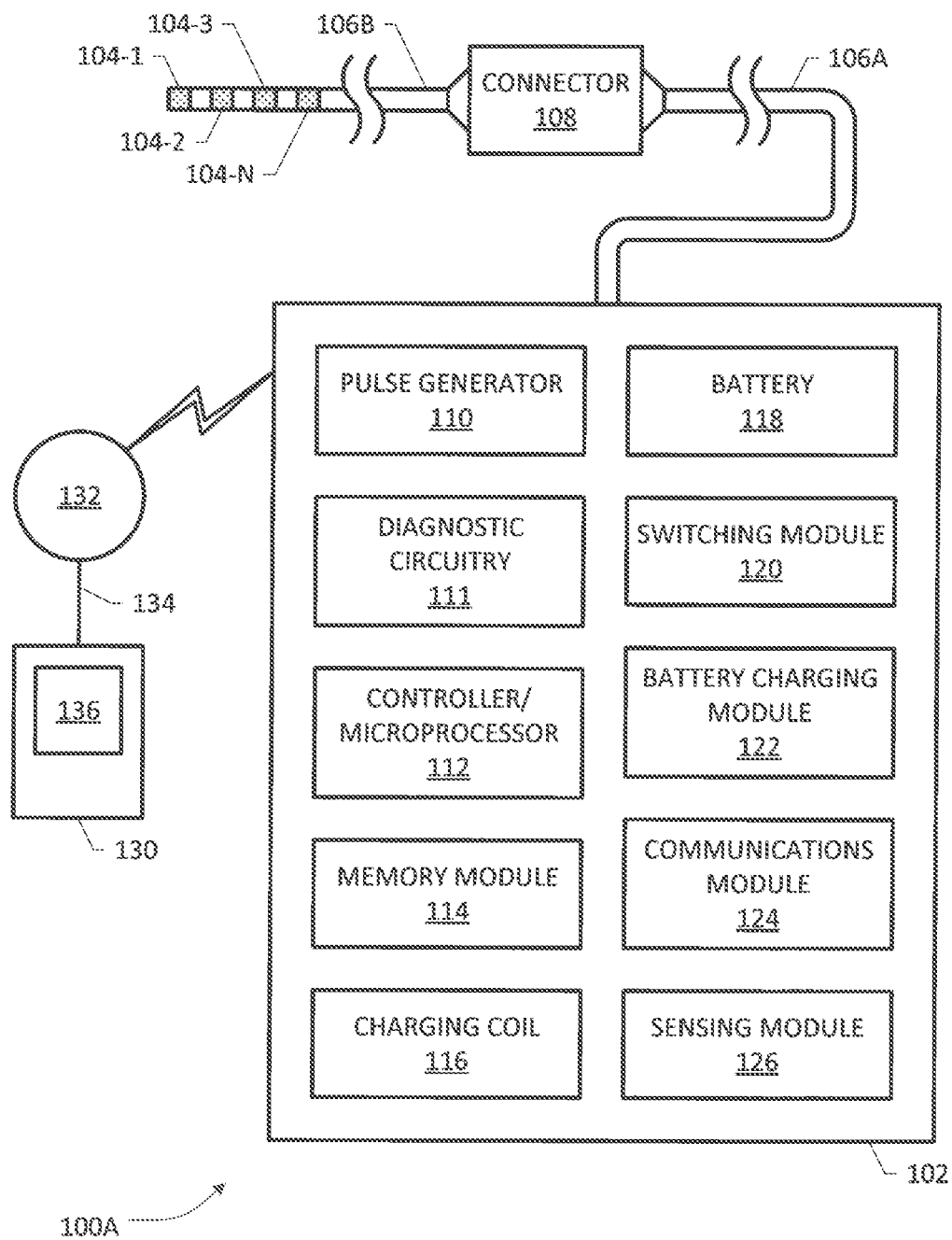
FIG. 1A depicts an example biostimulation system wherein one or more embodiments of an adjustable capacitive voltage multiplier (CVM) of the present disclosure may be practiced in association with an implantable medical device (IMD) for effectuating intra-pulse voltage multiplier control in a stimulation application according to the teachings herein.

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some embodiments described herein may be particularly set forth with respect to an implantable pulse generator (IPG) for generating electrical stimulation for application to a desired area of a body or tissue based on a suitable stimulation therapy application, such as a spinal cord stimulation (SCS) system. However, it should be understood that example circuitry and methods of operation disclosed herein are not limited thereto, but have broad applicability, including but not limited to different types of implantable devices such as neuromuscular stimulators and sensors, dorsal root ganglion (DRG) stimulators, deep brain stimulators, cochlear stimulators, retinal implanters, drug delivery systems, muscle stimulators, tissue stimulators, cardiac stimulators, gastric stimulators, and the like, including other bioelectrical sensors and sensing systems, which may be broadly referred to as "biostimulation" applications and/or implantable medical devices (IMDs) for purposes of the present disclosure. Moreover, example circuitry and methods of operation disclosed herein are not limited to use with respect to an IPG or any particular form of IPG. For example, some embodiments may be implemented with respect to a fully implantable pulse generator, a radio frequency (RF) pulse generator, an external pulse generator, a micro-implantable pulse generator, inter alia.

Referring to FIG. 1A in particular, depicted therein is a biostimulation system 100A wherein one or more embodiments of a real-time adjustable capacitive voltage multiplier (CVM) of the present disclosure may be practiced in association with an implantable medical device (IMD) for achieving optimized electrical performance in a stimulation application according to the teachings herein. By way of illustration, system 100A may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as noted above. System 100A comprises an implantable pulse generator (IPG) or IMD 102 having a pulse generator portion that is adapted to include or otherwise interoperate with a CVM and appropriate diagnostic circuitry for generating adjustable target voltages that may be selectively applied during the delivery of a single therapy pulse using a current regulator for intra-pulse optimization as will be set forth in additional detail hereinbelow. In one example embodiment, IMD 102 may be implemented as having a metallic housing or can that encloses a controller/processing block or module 112, pulse generating circuitry with current regulation module 110, a charging coil 116, a battery 118, a far-field and/or near field communication block or module 124, battery charging circuitry 122, switching circuitry 120, sensing circuitry 126, a memory module 114, and the like. Controller/processor module 112 typically includes a microcontroller or other suitable processor for controlling the various other components of IMD 102. Software/firmware code may be stored in memory 114, which may be integrated with the controller/processor module 112, and/or other suitable application-specific storage components (not particularly shown in this FIG.) for execution by the microcontroller or processor 112 and/or other programmable logic blocks to control the various components of IMD 102 for purposes of an embodiment of the present patent disclosure.

In one arrangement, IMD 102 may be coupled to a separate or an attached extension component 106A for providing electrical and physical connectivity to a lead system 106B via a lead connector 108, wherein a distal end of the lead 106B includes a plurality of electrodes 104-1 to 104-N. Where the extension component 106A is provided as a separate component, the extension component 106A may connect with a "header" portion of IPG/IMD 102 as is known in the art. If the extension component 106A is integrated with IMD 102, internal electrical connections may be made through respective conductive components. In general operation, electrical pulses are generated by the pulse generating circuitry 110 under the control of processing block 112 and are provided to the switching circuitry 120 that is operative to selectively connect to electrical outputs of the IMD, which are ultimately coupled to the electrodes 104-1 to 104-N at a distal end of the lead system 10B via respective electrical conductive traces.

In one arrangement, lead electrodes 104-1 to 104-N may be positioned along an axis of the lead 106B, with an angular offset such that the lead electrodes 104-1 to 104-N do not overlap. The lead electrodes 104-1 to 104-N may be in the shape of a ring such that each lead electrode continuously covers the circumference of the exterior surface of the lead 106B. Each of the lead electrodes 104-1 to 104-N are separated by non-conducting portions of the lead 106B, which electrically isolate each lead electrode 104-1 to 104-N from an adjacent lead electrode 104-1 to 104-N. The non-conducting portions of the lead 106B may comprise one or more insulative materials and/or biocompatible materials to allow the lead 106B to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane, or the like compositions.

Additionally, or alternatively, electrodes 104-1 to 104-N may be in the shape of a split or non-continuous ring such that the stimulation pulse(s) may be emitted in a manner so as to create an electric field emanating in an outward radial direction adjacent to the lead electrodes 104-1 to 104-N.

Examples of lead electrodes 104-1 to 104-N and associated fabrication processes are disclosed in one or more of the following: (i) U.S. Patent Application Publication No. 2011/0072657, entitled, "METHOD OF FABRICATING STIMULATION LEAD FOR APPLYING ELECTRICAL STIMULATION TO TISSUE OF A PATIENT," and (ii) U.S. Patent Application Publication No. 2018/0008821, entitled "IMPLANTABLE THIN FILM DEVICES," each of which is incorporated herein by reference.

It should be noted the lead electrodes 104-1 to 104-N may be in various other formations, for example, in a planar formation, in an array or grid, etc. on a paddle structure as disclosed in U.S. Patent Application Publication No. 2014/0343564, entitled, "PADDLE LEADS FOR NEUROSTIMULATION AND METHOD OF DELIVERYING THE SAME," which is incorporated herein by reference.

In one arrangement, the lead system 106B (including extension 106A where provided) may comprise a lead body of insulative material encapsulating a plurality of conductors within the material that extend from a proximal end (that is proximate to IMD 102) to the distal end of the lead body containing the lead electrodes 104-1 to 104-N. The conductors or conductive traces are operative to electrically couple the lead electrodes 104-1 to 104-N to a corresponding plurality of terminals (not shown) of the lead system 106A/B. In general, the terminals are adapted to receive electrical pulses from the pulse generation and switching circuitry of IMD 102, which are propagated via the corresponding conductive traces to at least a portion of the lead electrodes 104-1 to 104-N that are adapted to apply the pulses to a desired stimulation target of the patient depending on the particular stimulation therapy application. Also, sensing of physiological or bioelectrical signals may occur through the lead electrodes 104-1 to 104-N, corresponding conductors, and associated terminals. By way of illustration, an example embodiment of the stimulation system 100A may be provided with a plurality of lead electrodes 104-1 to 104-N comprising four electrodes, eight electrodes, etc., although any suitable number of electrodes (as well as corresponding conductive traces and terminals) may be provided in a lead system. Additionally, alternatively, or optionally, various sensors (e.g., a position detector, temperature sensor, one or more electrochemical sensors, a radiopaque fiducial, etc.) may be located near the distal end of the lead 106B and electrically coupled to terminals through associated conductors within the lead body.

Although not required for all embodiments, the lead body of the implantable lead system 106A/106B may be fabricated to flex and elongate upon implantation or advancing within or relative to the tissue (e.g., nervous tissue) of the patient towards the stimulation target to account for movement of the patient during or after implantation. Fabrication techniques and material characteristics for "body compliant" leads are disclosed in greater detail in U.S. Pat. No. 9,844,661, entitled "COMPLIANT ELECTRICAL STIMULATION LEADS AND METHODS OF FABRICATION," which is incorporated herein by reference.

An example implementation of the components within IMD 102, such as, e.g., processor and associated charge control circuitry for pulse generation, is described in U.S. Pat. No. 7,571,007, entitled "SYSTEMS AND METHODS FOR USE IN PULSE GENERATION," which is incorporated herein by reference. An example implementation of circuitry for recharging a rechargeable battery (e.g., battery charging circuitry 122) of an IMD using inductive coupling and external charging circuits is described in U.S. Pat. No. 7,212,110, entitled "IMPLANTABLE DEVICE AND SYSTEM FOR WIRELESS COMMUNICATION," which is incorporated herein by reference. Still further, an example implementation of "constant current" pulse generating circuitry (e.g., at least a portion of pulse generating circuitry 110) is provided in U.S. Patent Application Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG/IMD 102 operating in association with a current regulator for providing adjustable intra-pulse voltage multiplier control according to the teachings of the present disclosure as will be set forth in additional detail further below. In some example embodiments, different stimulation pulses on different lead electrodes selected from electrodes 104-1 to 104-N may be generated using consecutively generated pulses according to a "multi-stimset program" as is known in the art. Complex pulse parameters may be employed such as those described in U.S. Pat. No. 7,228,179, entitled "METHOD AND APPARATUS FOR PROVIDING COMPLEX TISSUE STIMULATION PATTERNS," and International Patent Publication Number WO 2001/093953, entitled "NEUROMODULATION THERAPY SYSTEM," which are incorporated herein by reference. Alternatively, multiple sets of such stimulation circuitry may be employed to provide high frequency pulse patterns (e.g., tonic stimulation waveform, burst stimulation waveform, and the like) that include generated and delivered stimulation therapy through one or more leads or electrodes 104-1 to 104-N as is also known in the art. Various sets of parameters may define the pulse characteristics and pulse timing for the pulses applied to the various lead electrodes as is known in the art. It should be appreciated that although constant current pulse generating circuitry is contemplated for some embodiments, any other suitable type of pulse generating circuitry may be employed in association with an adjustable CVM arrangement of the present invention.

In an example implementation of IMD 102, sensing circuitry 126 may be optionally provided, preferably adapted to measure a suitable electric parameter or transduced characteristic (e.g., voltage, current, capacitance, etc.) over a configurable time associated with the stimulation target or tissue through at least one of the electrodes proximate to the stimulation target. For example, the sensing circuitry 126 may measure an evoked compound activation potential (ECAP) waveform from an Aβ sensory fiber or spinal cord. Optionally, the sensing circuitry 126 may store the measured/sensed electric data in memory 114. Furthermore, diagnostic circuitry 111 may be configured to interoperate with the sensing circuitry 126 and pulse generation and switching functionalities of IMD 102 for generating suitable diagnostic control signals that may be configured to adjustably control the operation of a CVM for purposes of the present invention as will set forth further below in additional detail.

An external device 130 may be implemented to charge/recharge the battery 118 of IMD 102 (although a separate recharging device could alternatively be employed), to access memory 114, and/or to program or reprogram IMD 102 with respect to the stimulation set parameters including pulsing specifications while implanted within the patient. In alternative embodiments, however, separate programmer devices may be employed for charging and/or programming IMD 102 device and/or any programmable components thereof. An example embodiment of the external device 130 may be a processor-based system that possesses wireline and/or wireless communication capabilities, e.g., a tablet, smartphone, laptop computer, handheld computer, a personal digital assistant (PDA), or any smart wearable device and smart digital assistant device, etc. Software may be stored within a non-transitory memory of the external device 130, which may be executed by the processor to control the various operations of the external device 130. A connector or "wand" 134 may be electrically coupled to the external device 130 through suitable electrical connectors (not specifically shown), which may be electrically connected to a telemetry component 132 (e.g., inductor coil, RF transceiver, etc.) at the distal end of wand 134 through respective communication links that allow bi-directional communication with IMD 102. Optionally, in some embodiments, the wand 134 may comprise one or more temperature sensors for use during charging operations.

In general operation, a user (e.g., a doctor, a medical technician, or the patient) may initiate communication with IMD 102 by placing the wand 134 proximate to the stimulation system 100A. Preferably, the placement of the wand 134 allows the telemetry system to be aligned with the far-field and/or near field communication circuitry 124 of IMD 102. The external device 130 preferably provides one or more user interfaces 136 (e.g., touch screen, keyboard, mouse, buttons, scroll wheels or rollers, or the like), allowing the user to operate IMD 102. The external device 130 may be controlled by the user through the user interface 136, allowing the user to interact with IMD 102, including, e.g., effectuating programmatic control for dynamically configuring stimulation current pulses in some embodiments. Further, the user interface 136 may permit the user to move electrical stimulation along and/or across one or more of the lead(s) 106A/B using different lead electrode combinations selected from electrodes 104-1 to 104-N, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is incorporated herein by reference. Optionally, the user interface 136 may permit the user to designate which electrodes 104-1 to 104-N are to stimulate (e.g., emit current pulses, in an anode state, in a cathode state), or not selected to stimulate (i.e., remain inactive or floating), with respect to a potential stimulation target, to measure/sense tissue electrical parameters, or the like. Additionally, some electrodes of the lead system 106/A/B may be configured to operate as current sink terminals or cathodes whereas other electrodes may be configured as current source terminals or anodes. Additionally, or alternatively, the external device 130 may access or download the electrical measurements from the memory 114 acquired by the sensing circuitry 126.

In some embodiments, the external device 130 may permit operation of IMD 102 according to one or more stimulation therapy programs or applications (e.g., an SCS application) to treat the patient. Each therapy program may include one or more sets of stimulation parameters of the pulse including pulse amplitude, stimulation level, pulse width, pulse frequency or inter-pulse period, pulse repetition parameter (e.g., number of times for a given pulse to be repeated for respective stimulation sets or stimsets during execution of program), biphasic pulsing, monophasic pulsing, etc. IMD 102 may be configured to modify its internal parameters in response to the control signals from the external device 130 to vary the stimulation pulse characteristics of the stimulation therapy transmitted through the lead system 106A/106B to the tissue of the patient. Example neurostimulation (NS) systems, stimsets, and multi-stimset programs are set forth in U.S. Pat. No. 7,228,179, entitled "METHOD AND APPARATUS FOR PROVIDING COMPLEX TISSUE STIMULATION PATTERNS," and International Patent Publication Number WO 2001/093953, entitled "NEUROMODULATION THERAPY SYSTEM," which are incorporated hereinabove by reference.

Figure 1B:
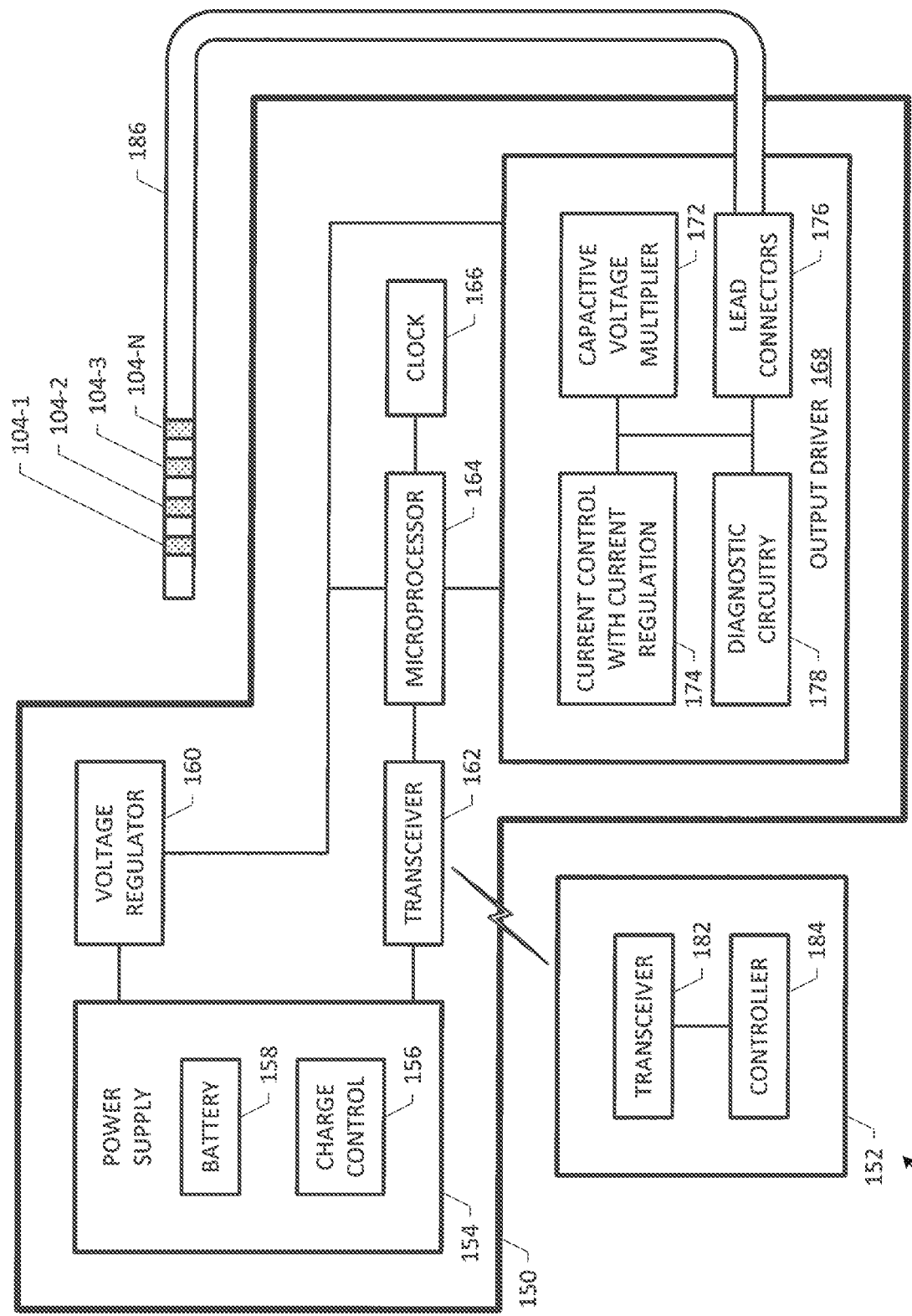
FIG. 1B depicts another view of a biostimulation system that illustrates additional details of an IMD's pulse generator configured to include an adjustable CVM according to an embodiment of the present disclosure.

FIG. 1B depicts another embodiment of a biostimulation system 100B that illustrates additional details of an example IMD's pulse generator configured to include an adjustable CVM in association with diagnostic circuitry to generate intra-pulse control signals according to an embodiment of the present disclosure. Stimulation system 100B is adapted to include a generator portion, shown as IPG 150, providing a stimulation or energy source, a stimulation portion, shown as lead system 186 for application of the stimulus pulse(s) similar to the lead system 106A/B described above, and an optional external controller, shown as programmer/controller 152, to program and/or control IPG 150 via a wired/wireless communications link, similar to the external device 130 described in the foregoing sections. IPG 150 may be implanted within the body of a human or animal patient (not shown) for providing electrical stimulation from IPG 150 to a selected area of the body via lead 186 under control of external programmer/controller 152. It should be appreciated that although lead 186 is illustrated to provide a stimulation portion of stimulation system 100B configured to provide stimulation remotely with respect to the generator portion 150 of stimulation system 100B, a lead as described herein is intended to encompass a variety of stimulation portion configurations including, e.g., a microstimulator electrode disposed adjacent to a generator portion.

Furthermore, one skilled in the art will recognize that although example lead systems 186 and 106A/B shown in FIGS. 1A/1B are exemplified with a single implantable lead, the teachings herein are not necessarily limited thereto and an example embodiment of the present invention may involve a lead system comprising two or more implantable leads, with each lead having a plurality of electrodes, wherein different electrodes may be grouped into different channels in a stimulation application and stimulation current pulses may be mapped across a number of electrodes regardless of the channels or whether one or more leads are selected for stimulation.

IPG 150 may comprise a self-contained implantable pulse generator having an implanted power source such as a long-lasting or rechargeable battery. Alternatively, IPG 150 may comprise an externally-powered implantable pulse generator receiving at least some of the required operating power from an external power transmitter, preferably in the form of a wireless signal, which may be radio frequency (RF)-based, via inductive coupling, etc., as noted previously. IPG 150 of the illustrated embodiment includes a voltage regulator 160, power supply 154, transceiver 162, microcontroller (or microprocessor) 164, clock 166, and output driver circuitry 168 comprising a current regulator block 174, adjustable CVM 172 and diagnostic circuitry 178, which will be described in further detail below. Power supply 154 provides a source of power, such as from battery 158 (which may comprise a non-rechargeable battery, e.g., single use battery, a rechargeable battery, a capacitor, and/or like power sources), to other components of IPG 150, as may be regulated by voltage regulator 160 including and/or facilitating digitally-programmable analog voltage generation. Charge control 156 of an example embodiment of IPG 150 is operative to provide recharging management with respect to battery 158. Transceiver 162 of an example embodiment of IPG 150 is operative to provide data/control communication between microprocessor 164 and a controller 184 of external programmer/controller 152, via transceiver 182 provided therewith. Transceiver 162 of an example embodiment, in addition to or in the alternative to providing data/control communication, may provide a conduit for delivering energy to power supply 158 via RF or inductive recharging as previously noted.

Microprocessor/controller 164 provides overall control with respect to the operation of IPG 150, such as in accordance with a program stored therein or provided thereto by external programmer/controller 152. Output driver circuitry 168 may be configured to generate and deliver stimulation current pulses having suitable pulse characteristics to selected ones of electrodes 104-1 to 104-N under control of microcontroller 164. In general operation, for example, a voltage multiplier 172 and current control 174 may be controlled to deliver a constant current pulse of a desired magnitude/amplitude, duration, and frequency to a tissue load present with respect to particular ones of electrodes 104-1 to 104-N, which may be represented by a suitable electrode/tissue interface (ETI) circuit model for purposes of the present disclosure. Clock 166 preferably provides system timing information, such as may be used by microcontroller 164 in controlling system operation, as may be used by voltage multiplier 172 in generating a desired voltage, etc., described below in further detail.

Lead system 186 of the illustrated embodiment includes a lead body encapsulating a plurality of internal conductors coupled to lead connectors (not shown) to interface with lead connectors 176 of IPG 150 in a hermetically sealed arrangement. The internal conductors provide electrical connection from individual lead connectors to each of a corresponding one of electrodes 104-1 to 104-N, which may be configured to provide anodic current stimulation and/or cathodic current stimulation for application at, or proximate to, a spinal nerve or peripheral nerve, brain tissue, muscle, or other tissue depending on a desired therapy. IPG 150 may be configured to control the electrical signals by varying signal parameters such as intensity, duration and/or frequency in order to deliver a desired therapy and/or otherwise provide stimulation current pulsing operations as described herein.

Skilled artisans will recognize that any number of electrodes, and corresponding conductors, may be utilized according to some embodiments, as previously noted. Moreover, various types, configurations and shapes of electrodes (and lead connectors) may be used according to some embodiments. An optional lumen (not shown) may extend through the lead 186, such as for use in delivery of chemicals or drugs or to accept a stylet during placement of the lead within the body of a patient. Additionally, or alternatively, the lead (stimulation portion) and IPG (generator portion) may comprise a unitary construction, such as that of a microstimulator configuration.

As mentioned above, programmer/controller 152 of an example embodiment provides data communication with IPG 150, such as to provide control (e.g., adjust stimulation settings), provide programming (e.g., selection and/or electrical polarity configuration of the electrodes to which stimulation pulses are delivered), etc. An embodiment of a pulse generation system and the delivery of stimulation pulses that may be configured to interoperate with the teachings herein may be found in U.S. Pat. No. 6,609,031, entitled "MULTIPROGRAMMABLE TISSUE STIMULATOR AND METHOD," which is hereby incorporated herein by reference.

In one example embodiment of IPG 150, voltage regulator 160 may be configured to accept a reference voltage $V_{REF}$, which may be prone to variation in magnitude, and provide an output voltage $V_{OUT}$ having a selected, relatively constant magnitude. For example, $V_{REF}$ may be provided by battery 158 which may have a relatively high voltage when initially charged or put into service and the voltage may drop over the life or charge cycle of the battery. However, circuitry of IPG 150 may malfunction if a voltage applied thereto is not within particular limits, and the high and low voltage extremes associated with battery 158 may be outside of these limits in some instances. Accordingly, voltage regulator 160 may be configured to provide a regulated supply $V_{OUT}$ within a range acceptable to circuitry of IPG 150, including output driver circuitry 168 having current control and current regulation 174 for purposes of an example embodiment of the present disclosure.

In general operation, a typical voltage regulator is capable of maintaining an output voltage only when the reference voltage provided thereto is at least slightly higher than the output voltage. However, over the course of a battery's life or charge cycle, the voltage provided thereby may be reduced to a point too close to or below the $V_{OUT}$, causing the voltage regulator output voltage to also fall. In such a situation, therefore, the regulator can no longer provide the desired regulated output voltage. However, voltage regulator 160 of an embodiment may be adapted to provide a desired output voltage level even when a reference voltage provided by battery 158 drops below the desired output voltage.

In one example implementation, voltage regulator 160 may include a multiplexer having multiple voltage inputs that are at different levels of the battery voltage ($V_B$), which may be selected under programmatic control to provide a suitable voltage supply output for the components of IPG 150. Some embodiments may also implement a closed loop control system with respect to voltage regulator 160 in order to provide further voltage selection control in association with suitable control signaling. For example, sensing circuitry, such as may utilize an analog-to-digital converter (ADC) in making voltage measurements may be utilized according to a preferred embodiment to provide information with respect to the battery voltage, which may be used by a digital control system (e.g., supported by microcontroller 164) in order to provide appropriate control signals e.g., select signals, for controlling the output voltage of voltage regulator 160. Additional details regarding voltage regulation may be found in U.S. Patent Application Publication No. 2009/0048643, entitled "METHOD FOR PROVIDING MULTIPLE VOLTAGE LEVELS DURING PULSE GENERATION AND IMPLANTABLE PULSE GENERATING EMPLOYING THE SAME" (hereinafter "the '643 patent application publication"), which is hereby incorporated herein by reference.

Skilled artisans will recognize that although an embodiment of voltage regulation is set forth hereinabove, a variety of techniques and circuits may be provided for operation with an adjustable CVM arrangement described below in a particular implementation. Broadly, any suitable voltage regulator/multiplier arrangement may be adapted to provide dynamic voltage adjustment, which may be operative with a digitally-programmable analog voltage generator for providing a voltage level that may be used for generating a desired stimulation current level, wherein appropriate intra-pulse control signals may be generated for configurably and selectively adjusting the CVM circuitry during the pulse width of one or more pulses according to some example embodiments of the present disclosure.

Figure 2:
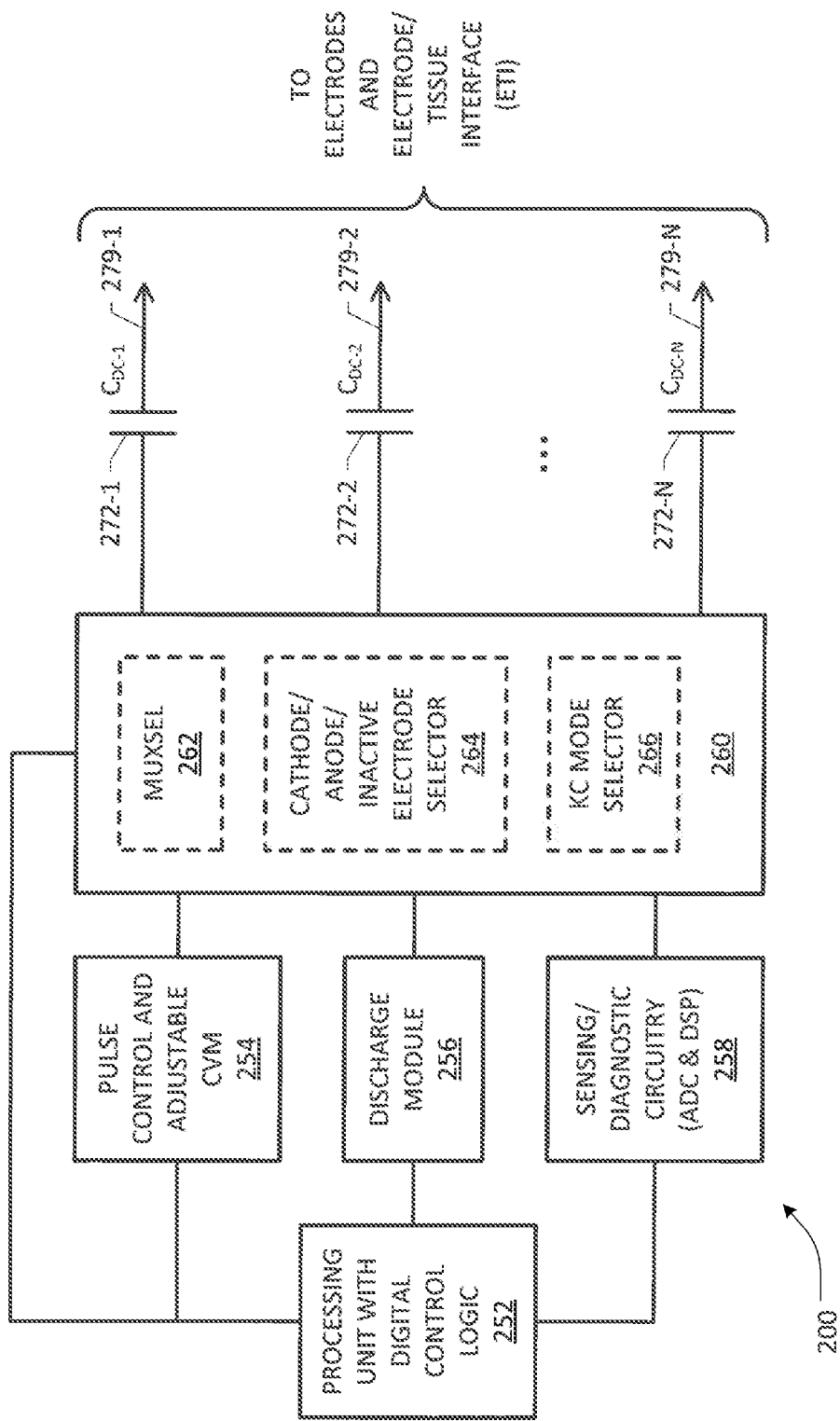
FIG. 2 depicts a block diagram of a pulse generator portion having diagnostic circuitry, adjustable CVM and associated lead electrode capacitor arrangement according to an embodiment of the present disclosure.

FIG. 2 depicts a block diagram of a pulse generator portion 200 having pulse control and adjustable CVM circuitry, diagnostic circuitry, and associated lead electrode capacitor arrangement according to an embodiment of the present disclosure. One skilled in the art will recognize upon reference hereto that various functionalities associated with example blocks shown as part of the pulse generator portion 200 may be distributed and/or integrated among one or more blocks, subsystems and/or modules described hereinabove with respect to FIGS. 1A/1B. Consistent with the description provided previously, a processing unit 252 having or associated with suitable digital control logic is operatively coupled to pulse control and CVM module 254, discharge module 256 and sensing/diagnostic circuitry 258 for facilitating various functionalities including but not limited to voltage measurements, active discharge cycling, electrode selection and configuration, intra-pulse control signal generation, etc. under appropriate programmatic/diagnostics control. An input/output (I/O) interface block 260 is operatively coupled to a plurality of lead connectors 279-1 to 279-N interfaced with respective electrodes and associated ETI arrangements that may be represented as circuitry based on known or heretofore unknown charge-transfer mechanisms or models (not shown in this FIG.). Each lead connector 279-1 to 279-N may be provided with a DC blocking stimulation capacitor ($C_{DC}$) for facilitating direct current flow blocking functionality with respect to the corresponding electrode that may be configured to operate as a stimulation node. Although some of the electrodes may also be configured to operate as sensing nodes in addition to providing stimulation (e.g., having an AC-coupling sense capacitor ($C_{SENSE}$) in addition to the DC blocking stimulation capacitor), such arrangements are not shown herein without loss of generality. By way of illustration, DC blocking stimulation capacitor $C_{DC\text{-}1}$ 272-1 is coupled to lead connector 279-1. Likewise, remaining lead connectors 279-N may be provided with respective $C_{DC\text{-}N}$ 272-N to facilitate DC blocking with respect to each corresponding lead electrode thereof.

Interface block 260 may include appropriate multiplexing and selection circuitry 262 and anode/cathode/inactive electrode selection circuitry 264 for measurement and sensing/diagnostics purposes wherein different electrodes of a lead system may be selectively configured for stimulation (e.g., anodic or cathodic stimulation), sensing, or designating unused/inactive states, etc., with appropriate electrical connections being made within an IPG device accordingly relative to the various components therein. In some embodiments, some portions of diagnostic circuitry 258 may comprise suitable analog-to-digital converter (ADC) circuitry configured for digital voltage measurement and associated signal processing using known voltage measurement techniques. As such, voltage measurement circuitry can be external and/or internal, on-board or off-board, and/or may be coupled to other measurement devices. Additional details regarding configuring lead electrodes as cathodes or anodes, either during stimulation or for discharging, may be found in may be found in the '643 patent application publication incorporated by reference hereinabove.

Figure 3:
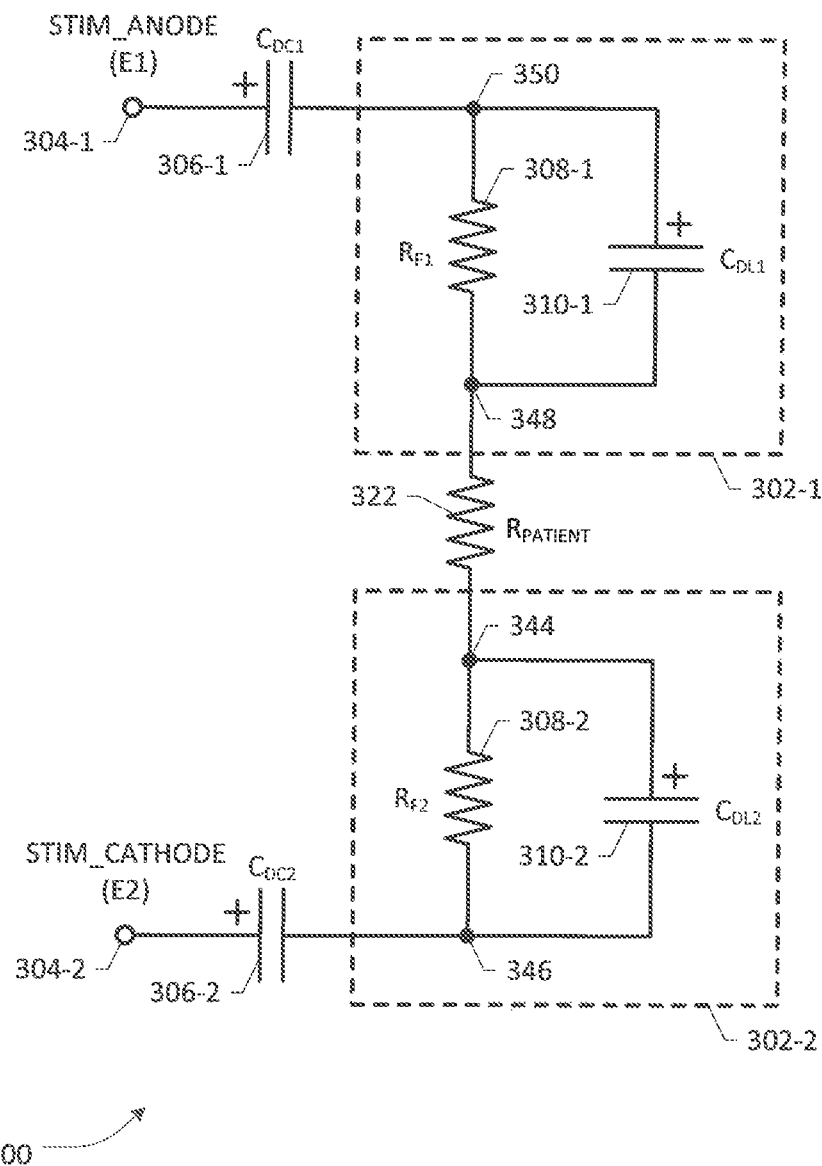
FIG. 3 depicts an example electrode/tissue interface (ETI) circuit representation in respect of an IMD's lead system where a constant current stimulation pulse may be applied to select electrode(s) according to an embodiment of the present disclosure.

When an electrode is placed near tissue, current flow is determined by the flow of electrons in the electrode and flow of ions in the tissue. The electrode/electrolyte (i.e., tissue) interface (EEI or ETI; also sometimes referred to as electrode/patient interface or EPI) is typically modeled in accordance with a linear lumped element charge transfer model involving a series of lumped resistor elements coupled with a shunt capacitance that models the double layer of charge at the interface. In an illustrative ETI circuit representation (e.g., as shown in FIG. 3 described further below), the solution resistance, $R_S$, is representative of the bulk electrolyte, which models the tissue or patient resistance, $R_{PATIENT}$. The double-layer capacitance or $C_{DL}$ models the double layer of charge at the interface of an electrode, which is coupled in parallel to a charge transfer resistance $R_F$ across the interface. The charge transfer resistance, $R_F$, in parallel with the capacitance, $C_{DL}$, accounts for the conduction of charge through the interface of the electrode, which can occur through various mechanisms, e.g., typically through oxidation-reduction reactions at the electrode for efficient operation of stimulation electrodes. Whereas more complex models of the electrode/tissue interface may be used, a charge transfer model is illustrated herein without necessarily being limited thereto for purposes of exemplifying how voltage measurements across a tissue load may vary during the pulse width of a constant current stimulation pulse applied to a patient's tissue during therapy.

Reference numeral 300 in FIG. 3 refers to an ETI circuit representation of two electrodes of a lead system where a constant current stimulation pulse may be applied to the patient's tissue, with one of the electrodes configured as an anode terminal (E1) 304-1 and the other electrode configured as a cathode terminal (E2) 304-2. Respective tissue interfaces 302-1 to 302-2 corresponding to E1 304-1 and E2 304-2 are shown by way of example. Each electrode is provided with a respective DC blocking stimulation capacitor $C_{DC}$, which facilitates a terminal or node with respect to an interface block coupled to pulse control circuitry and diagnostic/sense circuitry as described previously. Further, each ETI 302-1, 302-2 is exemplified by a corresponding $C_{DL1}$ 310-1, $C_{DL2}$ 310-2 coupled in parallel to respective charge transfer resistance $R_{F1}$ 308-1, $R_{F2}$ 308-2, that is in series connection with the bulk patient resistance $R_{PATIENT}$ 322 effectively disposed between ETI internal nodes 348, 344 of the electrodes 304-1 and 304-2. Respective $C_{DC1}$ 306-1, $C_{DC2}$ 306-2 may be coupled to ETI 302-1, 302-2 at corresponding internal nodes 350, 346. An example implementation of the inter-electrode ETI circuit representation 300 may comprise $C_{DC}$ capacitances around 20-30 µF whereas the $C_{DL}$ capacitances may be around 0.1-3.0 µF. Skilled artisans will also recognize that the $C_{DC}$ capacitance values may be even lower, e.g., around 10-15 µF, especially in smaller physical form factor implementations.

Figure 4:
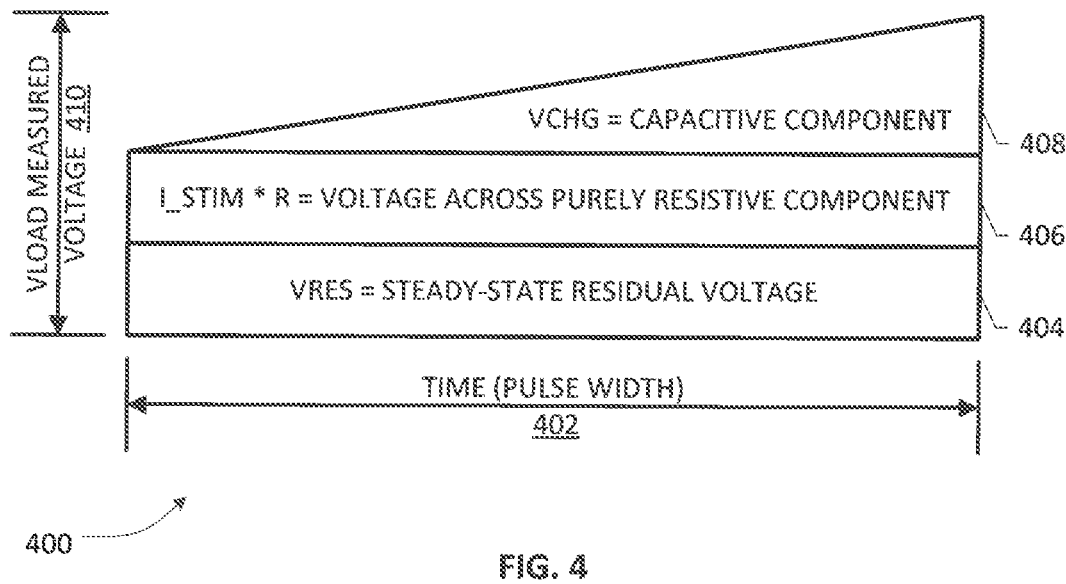
FIG. 4 depicts an example load voltage measurement across an ETI load during a pulse width of a constant current stimulation pulse applied to a patient's tissue in stimulation therapy.

The effect of a constant current pulse flowing through a pair of electrodes of a lead system is depicted in FIG. 4, wherein a load voltage waveform 400 across the resistive/capacitive load disposed between the electrodes (e.g., electrodes 304-1 and 304-2 of the ETI circuit representation of FIG. 3) during a pulse width is illustrated. Reference numeral 402 refers to a pulse width having a certain time duration (which may be a narrow pulse or a wide pulse depending on the stimulation program settings, e.g., on the order of a few µs to tens or hundreds of µs) during which a current pulse (I_STIM) having a select amplitude (e.g., having a fraction or multiple of a milliamp or mA) is applied to the patient's tissue at two electrodes 304-1 and 304-2 selected according to the stimulation therapy. VLOAD 410 represents the voltage measured/sensed across the electrodes 304-1 and 304-2, one of which may be a cathode terminal while the other may be an anode terminal. Consistent with the electrical characteristics of an ETI circuit representation, VLOAD 410 may be seen as formed of three components: a steady-state residual voltage (VRES) 404, an Ohmic component 406 due to a purely resistive component (determined by V=I_STIM×R) associated with the ETI model, and a capacitive component VCHG 408 (modeled as a monotonically rising function).

It will be appreciated that the average stimulation current drawn from an IMD's battery (e.g., battery 158 shown in FIG. 1B) in a constant current stimulation application based on using a capacitive voltage multiplier may be determined by the following equation:

$$IBATT\_AVG=I\_STIM*PW*F*VMULT\_FACTOR$$

where I_STIM=Pulse Amplitude;
PW=Pulse Width;
F=Stimulation Frequency; and
VMULT_FACTOR=Multiple/Division of Battery Voltage required for the pulse.

The VMULT_FACTOR may be determined by the voltage across the load (i.e., VLOAD) during the stimulation pulse, which is developed as a result of the IR drop, residual capacitor voltage and capacitive charging during the pulse as noted above. Whereas some implementations are capable of allowing the VMULT_FACTOR to be optimized for a pulse delivered in the therapy pattern based on measurements obtained in the previous pulses, such a technique is unsatisfactory for several reasons. First, VMULT_FACTOR is determined by the peak pulse voltage, which occurs at the end of the pulse and can differ significantly from the voltage required at the beginning of a long pulse. Also, multiple pulsing events or iterations of a stimulation program may be required to optimize each VMULT_FACTOR for adjusting the voltage to be used for the next pulsing event. In these implementations, diagnostic circuits of the IMD/IPG determine whether the VMULT_FACTOR is too high (i.e., excess current drawn from the battery) or too low (i.e., the pulse generator cannot deliver the programmed amplitude), and the VMULT_FACTOR is bumped up or down for the next time the pulse is delivered.

Even where a stimulation pattern is short and comprises only 4-8 unique pulses, there is still a delay before an adjusted VMULT_FACTOR may be applied. Further, the electrical conditions may have changed significantly when the next pulse is applied such that the adjusted VMULT_FACTOR may not be optimal for that pulse. In other words, it should be appreciated that selecting an VMULT_FACTOR that accommodates the voltage at the end of the pulse (for optimizing with respect to next pulses) can cause a CVM to generate voltages that are larger than necessary to be used for the earlier portion of the pulse waveform (as it takes longer to arrive at a more optimal setting down the pulse train because of having to wait for the whole pulse to lapse before resetting the CVM), thereby wasting battery energy.

In accordance with the teachings herein, embodiments of the present disclosure allow for the VMULT_FACTOR to be changed, increased, decreased or otherwise adjusted as the voltage (i.e., VLOAD) increases during the pulse so that less energy is wasted, resulting in a finer-grain adjustment for intra-pulse optimization. Further, repeated pulse cycles of a stimulation pulse train are not required for achieving optimization while a therapy program is applied to a patient. Accordingly, efficacious stimulation settings may be achieved relatively more quickly, allowing fewer pulses to be delivered from potentially sub-optimal settings.

Figure 5:
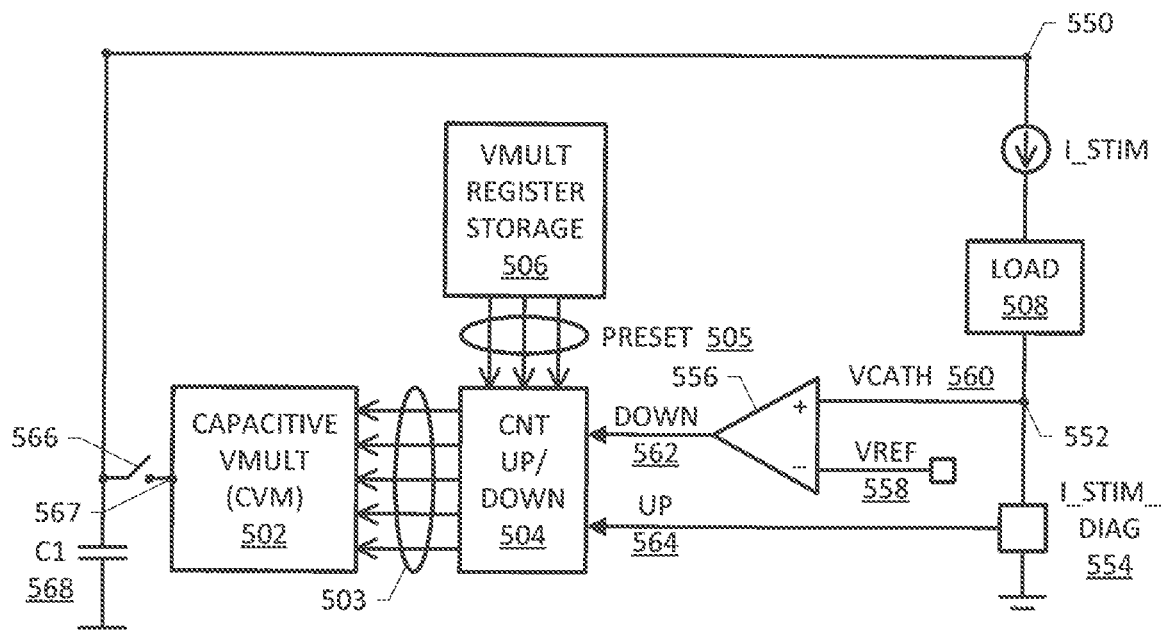
FIG. 5 depicts a block diagram of an adjustable CVM and associated diagnostic circuitry according to some embodiments of the present disclosure.

Turning attention to FIG. 5, depicted therein is a block diagram of an apparatus 500 including an adjustable CVM and associated diagnostic circuitry according to some embodiments of the present disclosure. In one embodiment, apparatus 500 may be provided with a VMULT storage register 506 operative to store an initial (or preconfigured) VMULT_FACTOR for each pulse that can be used to preset a CVM control counter 504 associated with a CVM 502. In some embodiments, the initial/preconfigured value may be optimized and used for the beginning of a therapy pulse so that CVM 502 doesn't have to change rapidly during the pulse rise time. The stimulation current may be controlled by a current regulator, which may be associated with a diagnostic circuit 554 that produces an UP control signal 564 when insufficient overhead voltage is available. Preferably, UP control signal 564 may be tuned to provide an early warning (e.g., within a guard band of the power supply rail voltage provided to the current regulator). Another diagnostic circuit 556 (e.g., which may be implemented as a comparator circuit in some embodiments) is operative to compare a cathode voltage 560 (VCATH) at a node 552 across a patient's tissue, represented as ETI load 508, to a programmable reference 558 to create a DOWN control signal. CVM control counter 504 may be configured as an UP/DOWN counter operative to modify the VMULT_FACTOR for CVM 502 in real-time (or substantially real-time) during the therapy pulse. Voltage output of CVM 502 is provided to an electrode configured to operate as an anode terminal 550 corresponding to the load 508, wherein the CVM output voltage is applied as an anodic voltage (VANODE). A switch 566 may be coupled to an output 567 of CVM 502 for facilitating disconnection of the CVM output 567 from VANODE terminal 550 during voltage adjustment transitions so as to ensure that a charge pump capacitor arrangement of the CVM (not shown in this FIG.) is properly reconfigured or restacked. An auxiliary voltage source 568, e.g., a capacitor of 1.0 nF or larger, may be switchably coupled to CVM 502 in order to maintain a voltage supply for stimulation during a transition time (when the CVM output 567 is disconnected) while a stimulation pulse is still being delivered.

In one arrangement, CVM control counter 504 is operative to generate an N-bit counter output signal 503 responsive to either a preset configuration value 505 (e.g., provided by way of a plurality of digital signals) loaded from VMULT storage register 506 or one of the control signals generated from the diagnostic circuitry, i.e., DOWN control signal 562 or UP control signal 564. Preferably, CVM 502 may be configured such that the charge pump arrangement provided therewith is operative responsive to the N-bit counter output signal 503 in order to cause either a decrease or an increase in a target voltage output of CVM 502 by a predetermined amount (e.g., a particular multiple or a fraction of a battery voltage). As noted above, comparator 556 is operative as a diagnostic circuit to generate the DOWN control signal 562 based on the input signals VCATH 560 and VREF 558. In one arrangement, comparator 556 may be implemented as a differential operational amplifier (op amp) having a single-ended output. Appropriate logic circuitry may be implemented such that the DOWN control signal 562 is generated as a binary signal which is asserted (i.e., logic high) if VCATH 560 is greater than VREF 558 or de-asserted (i.e., logic low) if VCATH 560 is lower than VREF 558. In general, DOWN control signal 562 may be configured to decrement the CVM control counter 504 so as to cause a decrease in a target voltage output of CVM 502 by a predetermined amount, e.g., a particular multiple or a fraction of a battery voltage.

Figure 6:
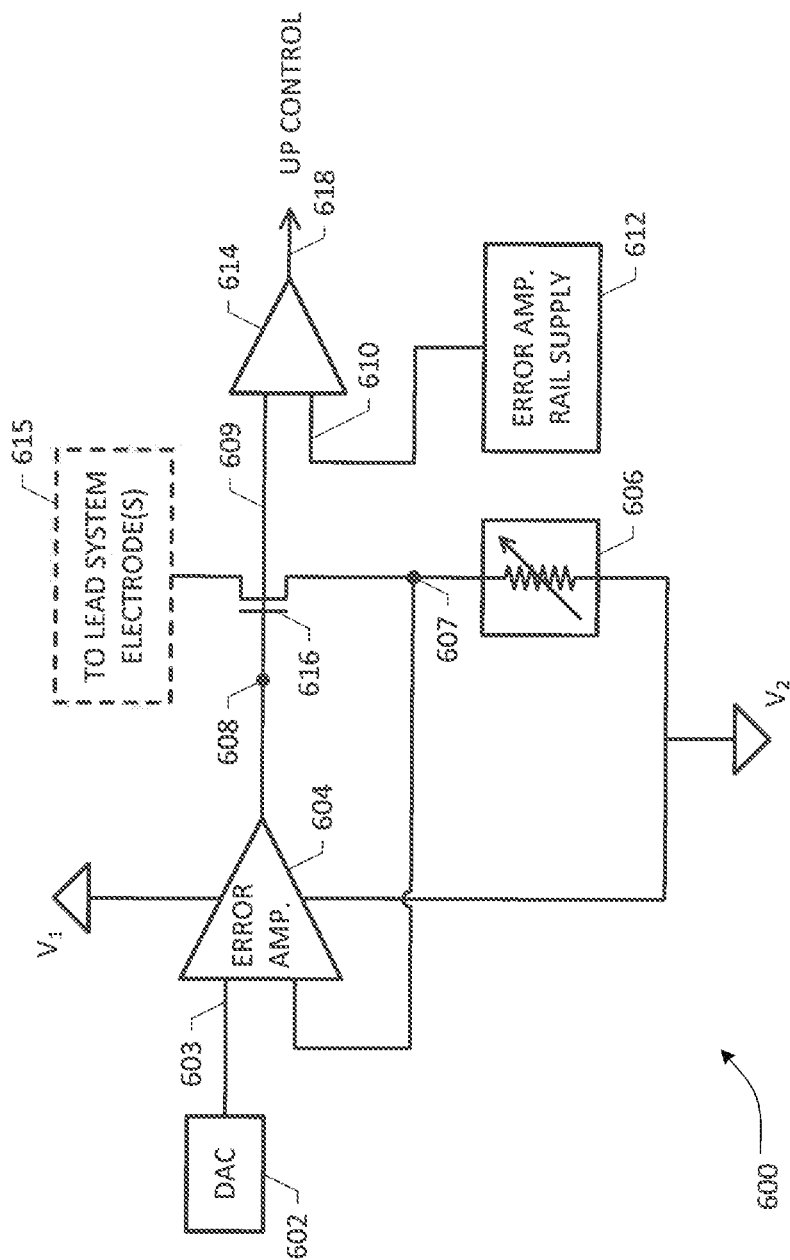
FIG. 6 depicts a block diagram of a diagnostic circuit associated with a current regulator according to some embodiments of the present disclosure.

In similar fashion, UP control signal 564 may be generated by the diagnostic circuit 554 associated with a current regulator operative to provide the stimulation current. FIG. 6 depicts a block diagram of an apparatus 600 including a current regulator and associated diagnostics circuitry according to some embodiments of the present disclosure. A digital-to-analog converter (DAC) 602 may be provided to interface with appropriate voltage supply (e.g., having suitable magnitude and polarity, depending on the type of stimulation current being programmed) to generate a digitally-programmed analog voltage level as an output signal 603, which may be provided to an error amplifier 604 having one or more power supply rail voltages. In one arrangement, the error amplifier 604 may be implemented as an op amp having two inputs for providing a differential input and operative with a pair of power supply rail voltage nodes, $V_1$ and $V_2$, that may be suitably biased depending on whether cathodic stimulation current or anodic stimulation current is being programmed. Accordingly, the digitally-programmed analog voltage signal (VDAC) 603 may be coupled to a first input of the error amplifier 604, wherein a second input is coupled to a programmable resistor network 606 operative to provide a digitally-programmed resistance (RSCALE) in a feedback loop arrangement for modulating a stimulation current output. In general operation, the error amplifier 604 may be programmatically configured to generate a desired amount of stimulation current (I_STIM), which may be set by the application of Ohm's Law In view of the digitally-programmed resistance RSCALE, where I_SITM=(VDAC/RSCALE), at a node 607 to which the programmable resistor network 606 is connected.

In one arrangement, a current conducting device 616 may be coupled to the node 607 for providing the stimulation current I_STIM to one or more lead system electrodes, generally shown at reference numeral 615. Device 616 may be controlled by an output node 608 of error amplifier 604. Further, a differential input comparator 614 may be configured to receive the error amplifier signal at node 608 as an input 609 for comparison with a power supply rail voltage 612 provided as an input 610 in order to generate an output signal 618, which may be provided to the CVM control counter 504 as the UP control signal 564 shown in FIG. 5. Similar to the operation of DOWN control signal 562, an UP control signal may be asserted as a logic high or logic low depending on the Boolean logic applied. In some embodiments, UP control signal 564 may be generated responsive to determining that the voltage at node 608 is within a predetermined range of a power supply rail voltage provided to the error amplifier 604 (i.e., current regulator) in order to provide a warning when a threshold overhead voltage is reached. In general, UP control signal 564 may be configured to increment the CVM control counter 504 so as to cause an increase in a target voltage output of CVM 502 by a predetermined amount (e.g., a particular multiple or a fraction of a battery voltage).

Skilled artisans will recognize that diagnostic circuits 554, 556 (which may be referred to as first and second diagnostic circuits or vice versa) may be implemented using other circuit elements and configurations. Also, such diagnostic circuits may be integrated together with other components of an IMD.

Figure 7:
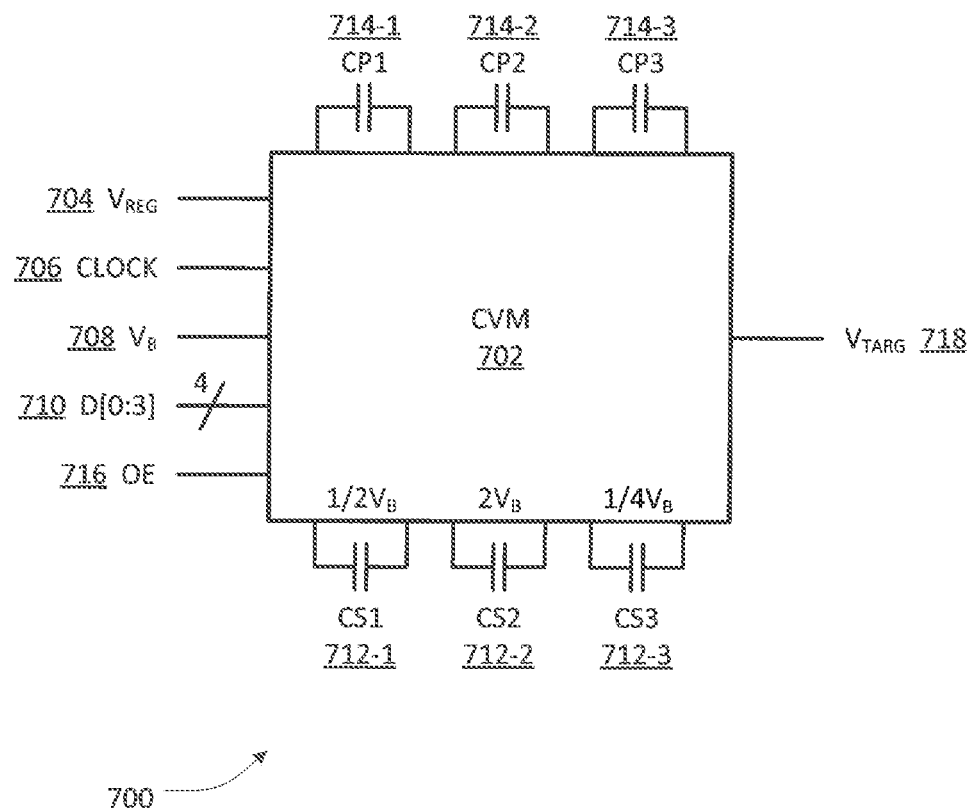
FIG. 7 depicts a high level block diagram of a voltage multiplier configuration operative to generate an adjustable target voltage at an output node according to some embodiments of the present disclosure.

FIG. 7 depicts a high-level block diagram of a voltage multiplier configuration 700 having an adjustable CVM 702 with a charge pump arrangement configured to generate an adjustable target voltage at an output node for purposes of an example embodiment of the present disclosure. Generally, a representative embodiment of voltage multiplier 700 may be configured to support power supply voltage multiplier and/or divider elements in a binary ladder distribution to provide a desired number of output voltage steps using a circuit design which may readily be implemented in a single integrated circuit (IC) or multiple ICs. For example, a capacitive voltage multiplier provided according to a representative embodiment may be operative as a DC-to-DC voltage conversion system comprising a voltage doubler generating twice the battery voltage, the battery itself generating the battery voltage, a voltage halver generating half of the battery voltage, and a voltage quarterer generating a quarter of the battery voltage, and/or any other fractional/multiples thereof. Accordingly, circuitry of the foregoing voltage multiplier configuration preferably operates to combine the different voltages to provide a range of output voltages In multiple steps, e.g., one-quarter battery voltage (¼ $V_{BATT}$ or $V_B$), or other power source voltage steps. By using such different sources in various combinations and/or by "stacking" these different sources in various ways, the voltage multiplier circuit may be used to provide desired voltages over a suitable range. For example, the output voltage of such a voltage multiplier may range from ¼ $V_B$ to 3¾ $V_B$, in one-quarter battery voltage steps in an example implementation.

In FIG. 7, voltage multiplier 700 of the illustrated embodiment includes CVM 702 implemented as an IC or other monolithic chip device, a first plurality of pump capacitors CP1 714-1, CP2 714-2, and CP3 714-3, and a second plurality of storage capacitors CS1 712-1, CS2 712-2, and CS3 712-3. CVM 702 is preferably operative responsive to signal inputs $V_{REG}$ 704, CLOCK 706, $V_B$ 708, an N-bit control signal 710, (e.g., a 4-bit signal D[0:3], which may be controlled and/or otherwise configured by a control counter such as UP/DOWN counter 504 of FIG. 5) and an output enable (OE) signal 716, in order to generate a target output voltage ($V_{TARG}$) at an output node or pin 718.

$V_{REG}$ 704 of the illustrated embodiment provides a regulated voltage input for use by circuits (e.g., digital control circuits) of CVM 702 in providing voltage multiplication. In an example implementation, $V_{REG}$ 704 is typically at a logic level (e.g., 2.2 volts) that is lower than the power supply voltage (e.g., $V_B$ 708). CLOCK 706 is a system clock signal used for synchronizing operation of aspects of CVM 702 with operation of aspects of a host system (e.g., IMD/IPG of a biostimulation system), such as for digital communication, voltage output timing, etc. $V_B$ 708 provides a power supply voltage level input for use in voltage fractional multiplication by CVM 702. For example, $V_B$ 708 may provide unregulated battery voltage input, such as 4.1 volts where a lithium-ion battery is used. D[0:3] 710 provides a nibble-wide digital input signal, which may be used in the illustrated embodiment for selecting a desired output voltage level. OE 716 is operative to selectively enable the output voltage ($V_{TARG}$) at output node 718. Accordingly, a signal provided at OE 716 may comprise a binary logic level signal which may be asserted at appropriate times (e.g., depending on the CLOCK signal 706).

Pump capacitors CP1 714-1, CP2 714-2, and CP3 714-3 of the illustrated embodiment may be utilized in a voltage generation cycle. Because of the use of a partitioned circuit configuration of CVM 702 of a representative embodiment (and due to the relatively low voltages experienced by capacitors CP1 714-1, CP2 714-2, and CP3 714-3 in an example implementation), the pump capacitors may be relatively small, such as on the order of 0.5 μF. One or more storage capacitors CS1 712-1, CS2 712-2, and CS3 712-3 may be configurably stacked in providing a desired output voltage ($V_{TARG}$). Moreover, in order to sustain a relatively constant (i.e., flat) output voltage level during a voltage output cycle, storage capacitors CS1 712-1, CS2 712-2, and CS3 712-3 may be larger than the pump capacitors, such as on the order of 100 μF. Accordingly, various capacitors utilized in generating a particular voltage multiple or voltage fraction need not be matched in implementing a particular charge pump arrangement of CVM 702. For example, according to a representative embodiment where pump capacitors are used in combination with storage capacitors to generate a voltage multiple or voltage fraction, the capacitors are not necessarily matched.

It should be appreciated that through controlled stacking of the various storage capacitors in providing a desired output voltage, the maximum voltage levels experienced by particular capacitors (and other components) may be minimized. Therefore, one or more of the capacitors or other circuitry may be sized differently with respect to one another according to some embodiments. Accordingly, various ones of the pump capacitors may be sized differently with respect to other pump capacitors and/or various ones of the storage capacitors may be sized differently with respect to other storage capacitors. Skilled artisans will therefore recognize that various charge pump capacitor configurations may be implemented in additional or alternative embodiments for purposes of the present patent disclosure.

In operation according to a representative embodiment, CVM 702 provides selectable voltage output at $V_{TARG}$ node 718 in various increments, e.g., from $0V_B$ to $3\frac{3}{4} V_B$ in $\frac{1}{4} V_B$ steps. In one implementation, a logic low input at OE 716 may be used to turn the voltage output at $V_{TARG}$ node 718 off (i.e., $0 V_B$), such as during a voltage generation or refresh cycle. A logic high input at OE 716 in combination with a particular nibble-wide bit combination logic input at D[0:3] may be used to turn the voltage output at $V_{TARG}$ node 718 on and select a particular voltage level from $\frac{1}{4} V_B$ to $3\frac{3}{4} V_B$ by appropriately configuring at least a portion of the charge pump capacitors. Other fractional voltages may be provided through the use of combinations of capacitors different than those of the exemplary embodiment shown in FIG. 7.

Generation of voltages using a voltage multiplier/conversion circuit such as the representative circuit 700 shown in FIG. 7 may include a plurality of phases, wherein an output of the voltage multiplier/conversion circuit may be disabled during one or more such phases. For example, a charge phase may be used to charge the pump capacitors with current from the power supply and a pump phase may be used to pump the current into storage capacitors (the combination of these phases being referred to as a generation phase). A source phase may be used to output a desired voltage using an appropriate configuration of pump capacitors and/or storage capacitors based on the D[0:3] logic (i.e., charge pump capacitors). Additional details regarding example interconnection or configuration of pump and storage capacitors in a charge phase and a pump phase, as well as selection of different output voltages ($V_{TARG}$) using appropriate selection circuitry operating under the control of D[0:3] may be found in U.S. Pat. No. 8,446,212, entitled "PULSE GENERATOR HAVING AN EFFICIENT FRACTIONAL VOLTAGE CONVERTER AND METHOD OF USE," which is incorporated herein by reference.

Figure 8:
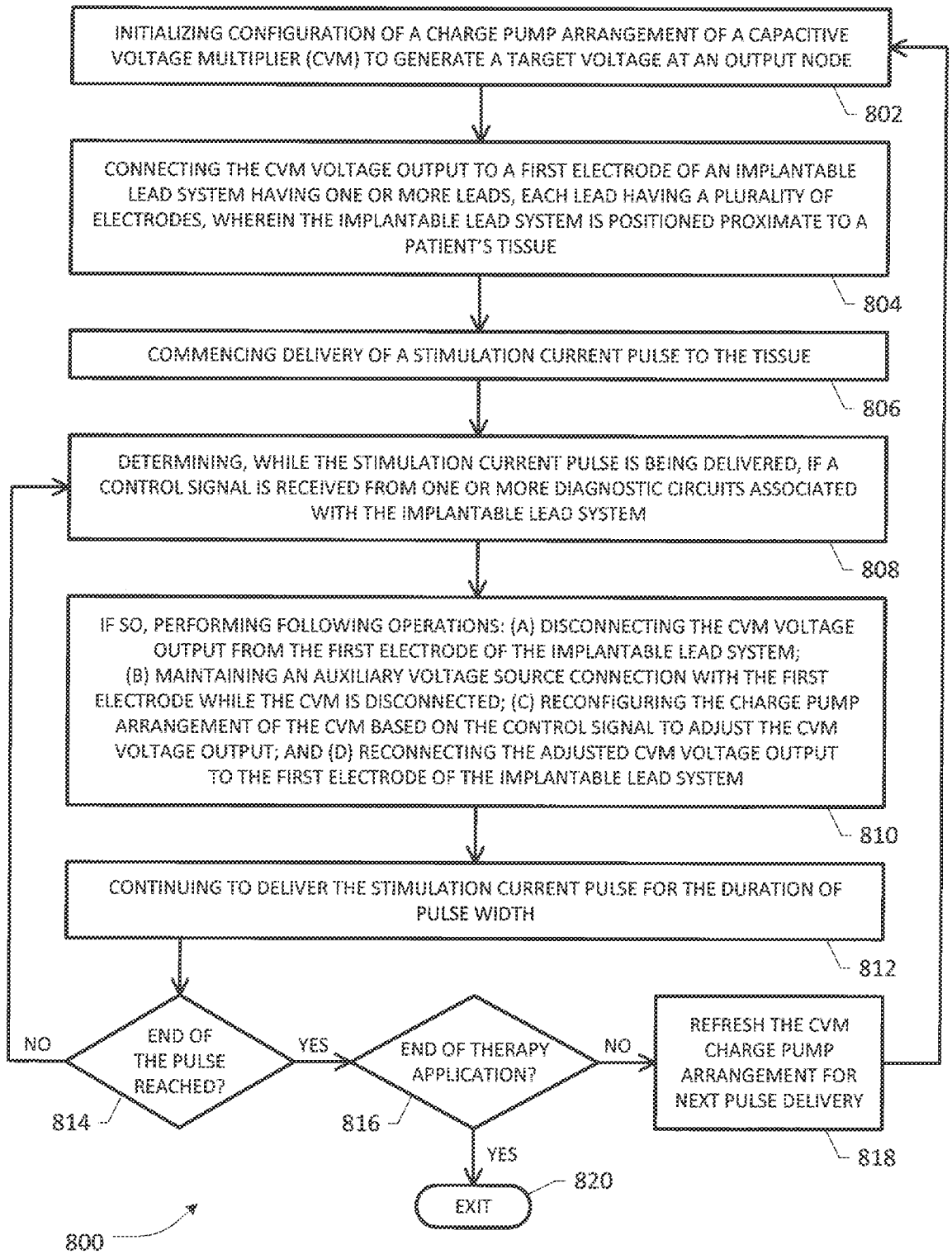
FIG. 8 depicts a flowchart of blocks, steps and/or acts that may be (re)combined in one or more arrangements with or without additional flowcharts of the present disclosure for facilitating adjustable intra-pulse voltage multiplier control according to some embodiments of the present disclosure.

FIG. 8 depicts a flowchart of blocks, steps and/or acts that may be (re)combined in one or more arrangements with or without additional flowcharts of the present disclosure for facilitating adjustable intra-pulse voltage multiplier control in an IMD according to some embodiments of the present disclosure. Example process 800 may commence with initializing a charge pump arrangement of a CVM (e.g., CVM 502/702 described above) disposed in the IMD to generate a target voltage at a CVM output node (e.g., node 718 shown in FIG. 7), as set forth at block 802. At block 804, the CVM output node is connected to a first electrode (e.g., VANODE) of an implantable lead system of the IMD, the implantable lead system having one or more leads, wherein each lead includes a plurality of electrodes and the implantable lead system is positioned proximate to a patient's tissue. At block 806, delivery of a stimulation current pulse to the tissue may be commenced. Responsive to determining at block 808 that a control signal is received from one or more diagnostic circuits associated with the implantable lead system of the IMD while the stimulation current pulse is being delivered, a plurality of operations may be performed. In an example embodiment, operation (a) may comprise disconnecting the CVM output node from the first electrode of the implantable lead system. Operation (b) may comprise maintaining an auxiliary voltage source connection with the first electrode during the time the CVM output node is disconnected while the stimulation current pulse is being delivered. Operation (c) may comprise reconfiguring the charge pump arrangement of the CVM based on the control signal (e.g., an UP or DOWN control signal) to adjust the target voltage to be output. Operation (d) may comprise reconnecting the CVM output node to provide an adjusted target voltage to the first electrode of the implantable lead system. These foregoing operations are exemplified at block 810. At block 812, the stimulation current pulse continues to be delivered for the duration of a pulse width. If the pulse has not reached its end (block 814), flow control loops back to monitoring and determining if additional control signals are generated by the diagnostic circuitry as set forth at block 808. Depending on the additional control signals, operations (a)-(d) may be repeated to adjust the CVM output voltage as needed. As noted above, for each output voltage adjustment, the CVM voltage output node is disconnected in order to allow the charge pump capacitors to be reconfigured.

At the end of the pulse, a further determination may be made as to whether the therapy application has reached its end (block 816). If so, process flow 800 may exit (block 820). Otherwise, the CVM is disconnected, and its charge pump capacitors may be refreshed for next pulse delivery at an appropriate time depending on the stimulation settings of the therapy application (block 818). In an example embodiment, the charge pump capacitors may be (re)configured or (re)initialized for the next pulse event based on a preset configuration value obtained from one or more previous pulse events. In one example arrangement involving the embodiment of FIG. 5, storage register 506 may be used for storing a preset value to be loaded into the CVM control counter 504 as the starting point for each pulse in a pulse train, which may be determined from the previous pulse event. In a further example where multiple prior pulse events are used in determining a preset configuration value, various capacitor stacking settings employed in generating the voltage adjustments (i.e., different $V_{TARG}$ values) during the prior pulsing events may be stored and analyzed by way of suitable statistical and/or machine leaning techniques in order to further optimize an initial setting such that a $V_{TARG}$ value is robustly optimized, resulting in a quicker settling time for achieving optimized therapy.

Figure 9:
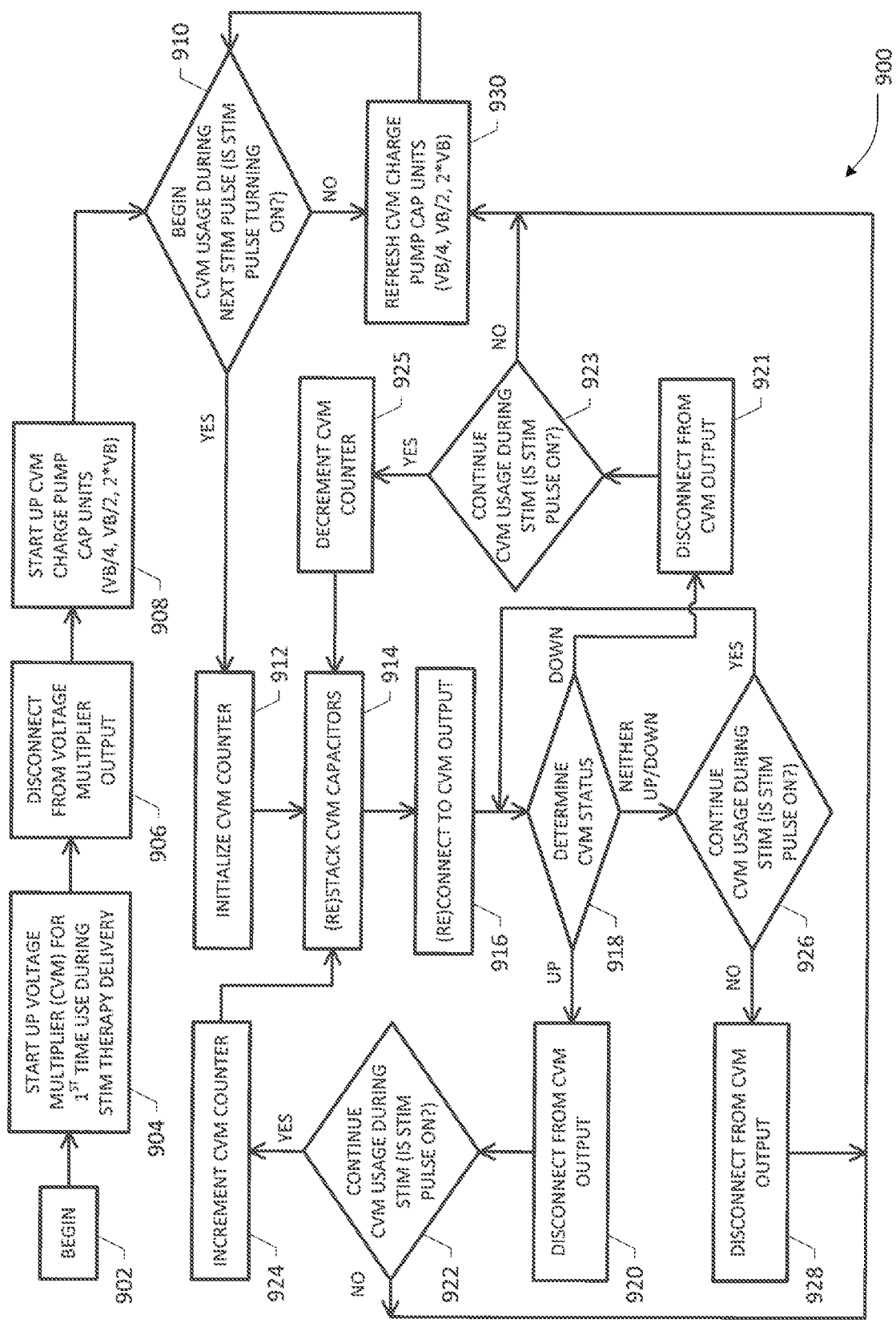
FIG. 9 depicts a flowchart of blocks, steps and/or acts that may be (re)combined in one or more arrangements with or without additional flowcharts of the present disclosure for facilitating adjustable intra-pulse voltage multiplier control according to some embodiments of the present disclosure.

FIG. 9 depicts a flowchart of another set of blocks, steps and/or acts that may be (re)combined in one or more arrangements with or without additional flowcharts of the present disclosure for facilitating adjustable intra-pulse voltage multiplier control in an IMD according to some embodiments of the present disclosure. Example process 900 may commence with initializing a CVM for the first time with respect to a stimulation therapy application, as set forth at blocks 902 and 904. As part of the initial start-up, the CVM's voltage output is disconnected from the lead electrode(s) selected a prior for stimulation (block 906). In one example implementation, a plurality of charge pump capacitors of the CVM may be refreshed at this stage so that any desirable combination of a target voltage may be generated (block 908). At block 910, a determination is made whether a logic signal for starting a stimulation pulse is ON, thereby indicating the CVM usage for the new (or next) pulse. If the CVM usage is indicated, a control counter is initialized, and the CVM's charge pump capacitors are (re)stacked accordingly, as set forth at blocks 912 and 914. If a stored preset configuration value is provided, that value may be loaded into the control counter which then generates an N-bit binary logic signal operative to configurably connect the charge pump capacitors as previously discussed. After the charge pump capacitors are (re)configured in accordance with the N-bit signal provided from the counter, the CVM's voltage output is (re)connected to the circuitry such that select stimulation electrode(s) are enabled to receive the stimulation pulse (I_STIM), as set forth at block 916. A determination as to the CVM status is made at block 918, i.e., to verify whether a control signal is received from the diagnostic circuitry. If an UP control signal or a DOWN control signal is received, the CVM output is disconnected as set forth in blocks 920, 921, respectively. A determination is made as to whether the stimulation pulse is being delivered (e.g., as may be determined by verifying if the logic signal associated with the stimulation pulse is still ON), as set forth at blocks 922, 923. If it is determined by either block 922 or 923 that the stimulation pulse is still being applied, the counter may be incremented (if an UP control signal was generated/received) or decremented (if a DOWN control signal was generated/received), as set forth at blocks 924 and 925, respectively. Depending on implementation, the granularity of voltage steps by which the CVM's output voltage may be increased or decreased may be the same, different, linear or non-linear, or otherwise configurable. After the counter value is adjusted accordingly, the CVM's charge pump capacitors are (re)configured as noted previously and the process of generating an adjusted output voltage and reconnecting with the lead electrode circuitry is iterated. If the stimulation pulse signal is not ON, as determined by either block 922 or 923, process flow 900 transitions to a CVM refresh stage 930, wherein the charge pump capacitors are recharged. Thereafter, flow control returns to block 910. If the pulse has reached its end (as determined by blocks 926 and 928), flow control also returns to block 930 (for refreshing) and block 910, whereupon a determination is made to commence the CVM usage for the next pulse event, as previously noted.

Figure 10:
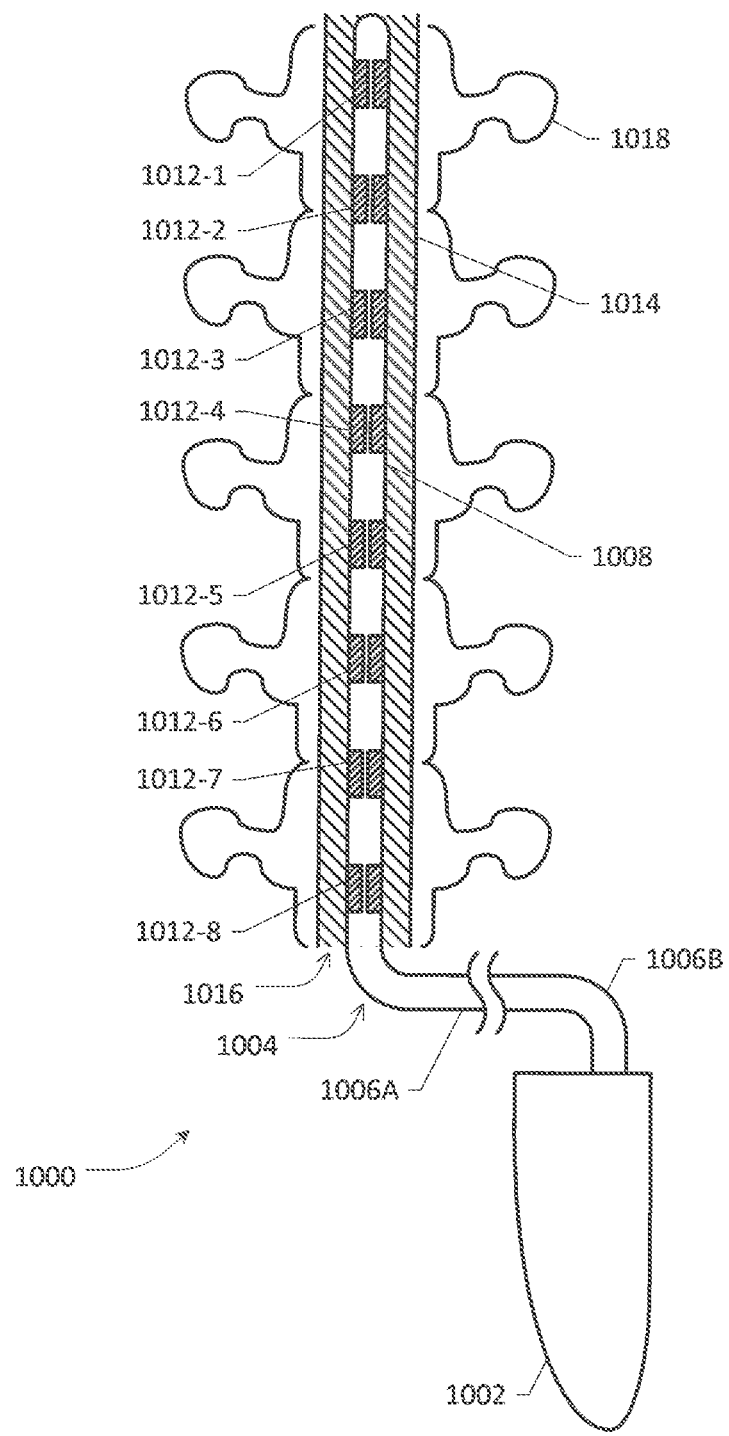
FIG. 10 illustrates an example spinal cord stimulation (SCS) therapy application involving an IMD and associated lead system having a plurality of electrodes that may be stimulated using an embodiment of the present disclosure.

FIG. 10 illustrates an example spinal cord stimulation (SCS) therapy application 1000 involving a pulse generator or IMD 1002 and associated lead system 1004 having a plurality of electrodes 1012-1 to 1012-8 wherein adjustable intra-pulse voltage multiplier control may be provided during a stimulation therapy according to an embodiment of the present disclosure. Preferably, the lead system 1004 comprises a lead body 1006A/B coupled to an implantable lead 1008 that may be positioned at a desired target position in an epidural space 1016 defined by a plurality of vertebrae 1018 of a patient so as to be in close proximity to a nerve tissue of interest, e.g., a spinal cord 1014. The implantable lead 1008 includes eight electrodes 1012-1 to 1012-8, which may comprise ring electrodes, segmented or split electrodes, and the like that may be separated from one another by equal or unequal portions of encapsulating material. The implantable lead 1008 is connected via lead body 1006A/1006B to IPG/IMD 1002 that includes at least an embodiment of a real-time adjustable CVM of the present disclosure that is configured to be operative with suitable diagnostic circuitry. As noted previously, at least a subset of the electrodes 1012-1 to 1012-8 may be selectively energized, i.e., stimulated, and appropriate constant current pulses may be applied wherein the overall stimulation current drawn the IMD's battery may be optimized based on intra-pulse voltage multiplier adjustments.

Figure 11A:
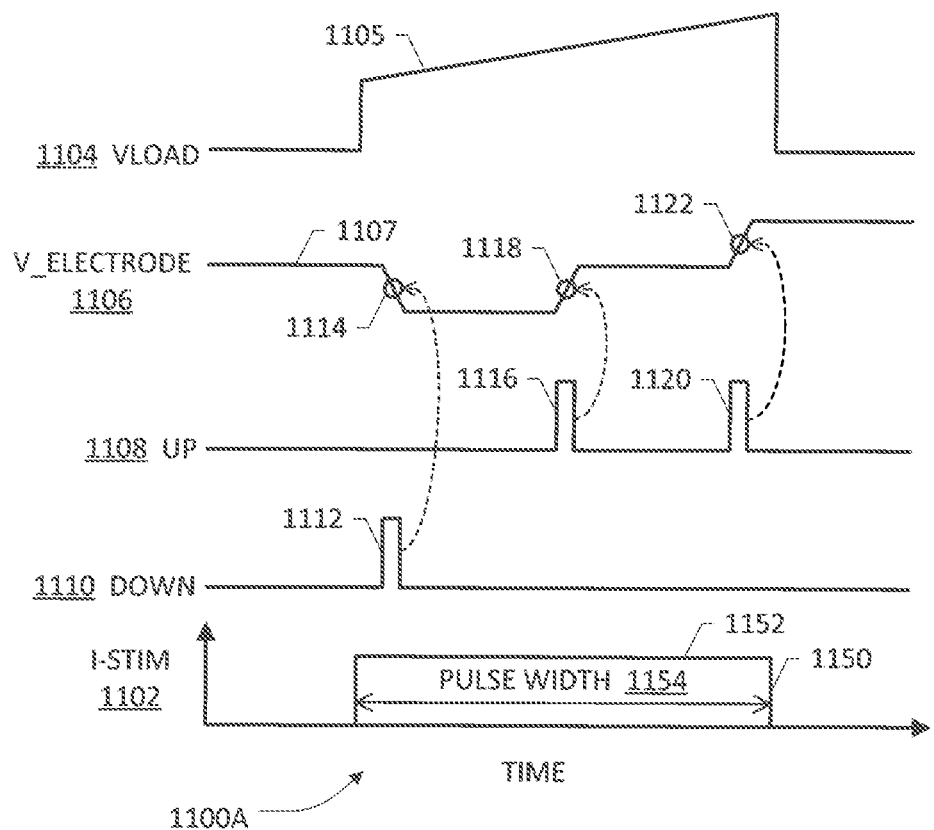
FIG. 11A depicts a panel of illustrative waveforms associated with various signals that may be generated during a stimulation current pulse according to some embodiments of the present disclosure.

FIG. 11A depicts a waveform panel 1100A illustrating a plurality of waveforms associated with various signals that may be generated during a stimulation current pulse according to some embodiments of the present disclosure. An I_STIM waveform 1102 illustrates a pulse 1150 having an amplitude 1152 and a width 1154 that is representative of a constant current pulse, which may be provided to a lead electrode as part of a stimulation therapy program. A VLOAD waveform 1104 corresponding thereto is shown as a ramped pulse 1105. A V_ELECTRODE waveform (e.g., VANODE) 1106 is exemplified as a signal that starts out at a particular level 1107 (e.g., depending on the initial configuration of the CVM), which may be ramped up or down depending on the occurrence of suitable control signals as described above. A DOWN control signal waveform 1110 is illustrated as having a single logic HIGH pulse 1112 that triggers a step-down ramp 1114 in the V_ELECTRODE signal 1106. Likewise, an UP control signal waveform 1108 is illustrated with two logic HIGH pulses 1116 and 1120, each of which causing a corresponding step-up ramp 1118 and 1122 in the V_ELECTRODE signal 1106. It should be appreciated that although multiple occurrences of a control signal assertion are shown within the duration of a single I_STIM pulse width, there may be only a single control signal asserted during the pulse width in some implementations. Further, there may not be an assertion of both UP and DOWN control signals within the same pulse in some implementations. Skilled artisans will recognize that the number and/or type of control signal assertions may depend on a number of factors. For example, in a therapy application having relatively long pulses (e.g., on the order of several μs), electrical conditions are more prone to change within a single pulse, which may therefore cause multiple control signal assertions and/or assertions of both UP and DOWN control signals within the same pulse.

Figure 11B:
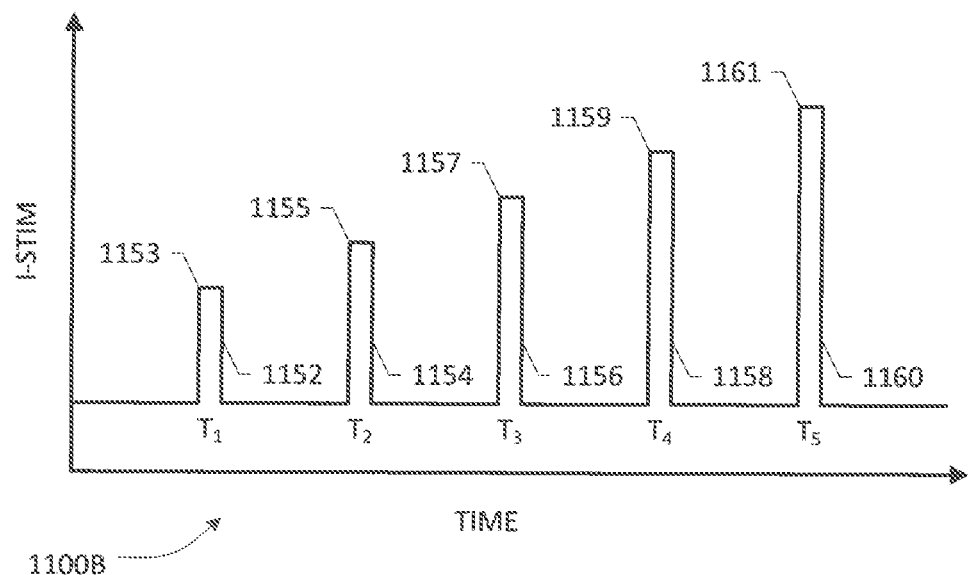
FIG. 11B depicts an example stimulation pulse train where adjustable control may be effectuated during delivery of a single therapy pulse according to some embodiments of the present disclosure.

FIG. 11B depicts an example stimulation pulse train 1110B where adjustable intra-pulse voltage multiplier control may be effectuated during delivery of a single therapy pulse according to some embodiments of the present disclosure. By way of example, five current pulses 1152-1160 are illustrated, each having a corresponding amplitude 1153-1161 and a corresponding pulse width, $T_1$-$T_5$.

Skilled artisans will appreciate that embodiments of a real-time adjustable CVM of the present invention may be used in association with either cathodic and anodic current regulators, which may be suitably configured to operate with respective current sources/sinks as well as current return paths in an IPG implementation, as is known in the art. For instance, depending on anodic or cathodic stimulation, the electrodes may be selectively tied to respective DAC circuitry configured to operate as current sources or current sinks in a current regulator arrangement, with appropriate diagnostic circuitry and CVM circuitry provided in accordance with the teachings herein. In one example implementation, an anodic current regulator arrangement may be formed of PMOS devices given that the source may be biased to a high voltage (V+), whereas a cathodic current regulator arrangement may be formed of NMOS devices where the sink is biased to a low voltage (V−), with respective substrate connections typically tied to a suitable power supply or to respective transistor source nodes. Other modifications as to, e.g., gate driver logic levels, device sizing (based on $I_{DS}$ handling requirements), among others, may be applied, mutatis mutandis, in a typical implementation depending on whether anodic or cathodic current stimulation architecture is involved.

In example embodiments of the present invention, the CVM diagnostic circuits may be optimized so that current delivery errors are skewed slightly early so as to avoid disturbing the output current pulse. Because of the ability to optimize the VMULT_FACTOR of a CVM for the entire duration of the pulse regardless of the pulse width, some of the advantages of the present invention may be particularly significant in the stimulation therapy applications involving long therapy pulses because when an UP control signal is received, the VMULT_FACTOR is immediately incremented and when a DOWN control signal is received, the VMULT_FACTOR is similarly immediately decremented. Further, embodiments herein may provide improved compatibility with randomized stimulation parameters (e.g., where the pulses are not identical and/or repeated in a predictable/deterministic fashion) since for this invention there is no need for such predictability or repetitiveness of pulses that is typically required for adjusting CVM output voltages only at the end of a pulse.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or nonvolatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Reference to an element in the singular is not intended to mean "one and only one" unless explicitly so stated, but rather "one or more." All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A method for providing adjustable voltage multiplier control in an implantable medical device (IMD), the method comprising:
   initializing a charge pump arrangement of a capacitive voltage multiplier (CVM) disposed in the IMD to generate a target voltage at a CVM output node;
   connecting the CVM output node to a first electrode of an implantable lead system of the IMD, the implantable lead system having one or more leads, wherein each lead includes a plurality of electrodes and the implantable lead system is positioned proximate to a patient's tissue;

commencing delivery of a stimulation current pulse to the patient's tissue; and responsive to determining that a control signal is received from one or more diagnostic circuits associated with the implantable lead system of the IMD while the stimulation current pulse is being delivered, performing following operations:

(a) disconnecting the CVM output node from the first electrode of the implantable lead system;

(b) maintaining an auxiliary voltage source connection with the first electrode while the CVM output node is disconnected;

(c) reconfiguring the charge pump arrangement based on the control signal to adjust the target voltage to be output; and (d) reconnecting the CVM output node to provide an adjusted target voltage to the first electrode of the implantable lead system.

2. The method as recited in claim 1, wherein the charge pump arrangement comprises a plurality of capacitors configurably connectable responsive to an N-bit counter output signal from a control counter operative based on the control signal and the charge pump arrangement is initialized in response to a preset configuration value loaded from a register storage into the control counter.

3. The method as recited in claim 2, further comprising providing a storage capacitor to operate as the auxiliary voltage source connection with the first electrode for maintaining a voltage supply while the CVM is disconnected during the stimulation current pulse.

4. The method as recited in claim 3, wherein a DOWN signal is provided as the control signal to the control counter responsive to determining that a voltage at a second electrode of the implantable lead system operative as a return terminal across the patient's tissue is greater than a reference voltage.

5. The method as recited in claim 4, wherein the DOWN signal is operative to decrement the control counter to cause a decrease in the target voltage by a first predetermined amount.

6. The method as recited in claim 3, wherein an UP signal is provided as the control signal to the control counter responsive to determining that a voltage at an output node of a current regulator of the IMD is within a range of a power supply rail voltage provided to the current regulator.

7. The method as recited in claim 6, wherein the UP signal is operative to increment the control counter to cause an increase in the target voltage by a second predetermined amount.

8. The method as recited in claim 1, further comprising:

continuing to deliver the stimulation current pulse to the implantable lead system; and responsive to additional control signals received from the diagnostic circuits before the stimulation current pulse is ended, continuing to adjust the target voltage output from the CVM according to the additional control signals and applying corresponding adjusted target voltages to the first electrode of the implantable lead system by performing operations (a)-(d) for each adjustment.

9. The method as recited in claim 8, further comprising refreshing the charge pump arrangement of the CVM responsive to determining that the stimulation current pulse has ended.

10. The method as recited in claim 8, wherein the stimulation current pulse is generated according to a stimulation therapy program specifying a select set of pulse properties comprising at least one of a stimulation frequency, a stimulation pulse width, a stimulation pulse amplitude, a discharge method, and phase information.

11. An implantable medical device (IMD) configured to provide adjustable voltage multiplier control in stimulation therapy, the IMD comprising:

a capacitive voltage multiplier (CVM) having a charge pump arrangement configured to generate an adjustable target voltage at a CVM output node;

a control counter adapted to generate an N-bit counter output signal operative to configure the charge pump arrangement for facilitating adjustment of the target voltage generated at the CVM output node;

a register for storing a preset configuration value operative to be loaded into the control counter for initializing the charge pump arrangement;

a lead system comprising one or more leads configured to be positioned proximate to a patient's tissue, wherein each lead of the one or more leads includes a plurality of electrodes; and diagnostic circuitry operative to generate one or more control signals while a stimulation current pulse is being delivered to the lead system after the CVM output node having an initial target voltage is connected to a first electrode of the lead system, wherein a control signal is configured to cause:

(a) disconnecting the CVM output node from the first electrode of the lead system;

(b) maintaining an auxiliary voltage source connection with the first electrode while the CVM output node is disconnected;

(c) reconfiguring the charge pump arrangement based on incrementing or decrementing the N-bit counter output signal of the control counter to adjust the target voltage; and (d) reconnecting the CVM output node to provide an adjusted target voltage to the first electrode of the lead system.

12. The IMD as recited in claim 11, wherein the charge pump arrangement comprises a plurality of capacitors configurably connectable responsive to the N-bit counter output signal from the control counter.

13. The IMD as recited in claim 12, further comprising a capacitor selectably connectable as the auxiliary voltage source connection with the first electrode for maintaining a voltage supply while the CVM is disconnected during the stimulation current pulse.

14. The IMD as recited in claim 13, wherein the diagnostic circuitry comprises a circuit for generating a DOWN signal operative as the control signal in response to determining that a voltage at a second electrode of the lead system operative as a return terminal across the patient's tissue is greater than a reference voltage.

15. The IMD as recited in claim 14, wherein the DOWN signal is operative to decrement the control counter to cause a decrease in the target voltage by a first predetermined amount.

16. The IMD as recited in claim 13, wherein the diagnostic circuitry comprises a circuit for generating an UP signal operative as the control signal in response to determining that a voltage at an output node of a current regulator of the IMD is within a range of a power supply rail voltage provided to the current regulator.

17. The IMD as recited in claim 16, wherein the UP signal is operative to increment the control counter to cause an increase in the target voltage by a second predetermined amount.

18. The IMD as recited in claim 13, wherein the stimulation current pulse is generated according to a stimulation therapy program specifying a select set of pulse properties comprising at least one of a stimulation frequency, a stimulation pulse width, a stimulation pulse amplitude, a discharge method, and phase information.

19. A non-transitory storage medium having program code stored thereon that facilitates, when executed by a processor of an implantable medical device (IMD), adjustable voltage multiplier control in stimulation therapy provided to a patient's tissue, the program code configured to:
   initialize a charge pump arrangement of a capacitive voltage multiplier (CVM) disposed in the IMD to generate a target voltage at a CVM output node;
   connect the CVM output node to a first electrode of an implantable lead system of the IMD;
   commence delivery of a stimulation current pulse to the patient's tissue; and
   responsive to determining that a control signal is received from one or more diagnostic circuits associated with the implantable lead system of the IMD while the stimulation current pulse is being delivered, perform following operations:
      (a) disconnecting the CVM output node from the first electrode of the implantable lead system;
      (b) maintaining an auxiliary voltage source connection with the first electrode while the CVM output node is disconnected;
      (c) reconfiguring the charge pump arrangement based on the control signal to adjust the target voltage to be output; and
      (d) reconnecting the CVM output node to provide an adjusted target voltage to the first electrode of the implantable lead system.

20. The non-transitory storage medium as recited in claim 19, wherein the charge pump arrangement comprises a plurality of capacitors, the program code further comprising code for configurably interconnecting the plurality of capacitors responsive to an N-bit counter output signal generated from a control counter in response to the control signal operating as an UP control signal or a DOWN control signal.

* * * * *

UNITED STATES PATENT AND TRADEMARK OFFICE
CERTIFICATE OF CORRECTION

PATENT NO. : 11,154,714 B2
APPLICATION NO. : 16/520052
DATED : October 26, 2021
INVENTOR(S) : Daran DeShazo et al.

Page 1 of 1

It is certified that error appears in the above-identified patent and that said Letters Patent is hereby corrected as shown below:

In the Specification

Column 1, Line 36, delete "mufti-electrode" and replace with --multi-electrode--.
Column 1, Line 47, delete "property" and replace with --properly--.
Column 2, Line 60, delete "inter ala" and replace with --inter alia--.
Column 6, Line 42, delete "10B" and replace with --106B--.
Column 21, Line 1, delete "a prior" and replace with --a priori--.

Signed and Sealed this
Fourth Day of January, 2022

Drew Hirshfeld
*Performing the Functions and Duties of the
Under Secretary of Commerce for Intellectual Property and
Director of the United States Patent and Trademark Office*